United States Patent
Shannon et al.

(10) Patent No.: US 11,523,882 B2
(45) Date of Patent: Dec. 13, 2022

(54) SYSTEMS AND METHODS FOR MANUFACTURE OF ORTHODONTIC APPLIANCES

(71) Applicant: Braces On Demand Inc., Hicksville, NY (US)

(72) Inventors: Thomas Patrick Shannon, Byron Center, MI (US); Colin James Corey, Carlsbad, CA (US); Ammar Ahmed Syed, Unionville (CA)

(73) Assignee: BRACES ON DEMAND INC., Hicksville, NY (US)

( * ) Notice: Subject to any disclaimer, the term of this patent is extended or adjusted under 35 U.S.C. 154(b) by 300 days.

(21) Appl. No.: 16/875,618

(22) Filed: May 15, 2020

(65) Prior Publication Data
US 2020/0275992 A1 Sep. 3, 2020

Related U.S. Application Data

(60) Provisional application No. 62/931,679, filed on Nov. 6, 2019.

(51) Int. Cl.
*A61C 7/00* (2006.01)
*G16H 10/60* (2018.01)
(Continued)

(52) U.S. Cl.
CPC .......... *A61C 7/002* (2013.01); *A61C 13/0019* (2013.01); *G16H 10/60* (2018.01);
(Continued)

(58) Field of Classification Search
CPC ............... A61C 7/002; A61C 13/0019; A61C 2007/004; G16H 10/60; B33Y 50/00; B33Y 80/00
(Continued)

(56) References Cited

U.S. PATENT DOCUMENTS

| 4,038,753 A | 8/1977 | Klein |
| 5,975,893 A | 11/1999 | Chishti |

(Continued)

OTHER PUBLICATIONS

PCT; App. No. PCT/US20/58482; International Search Report and Written Opinion dated Feb. 4, 2021.

*Primary Examiner* — Hai Tao Sun
(74) *Attorney, Agent, or Firm* — Nixon Peabody LLP

(57) ABSTRACT

In some embodiments, apparatuses and methods are provided herein useful to providing data files associated with orthodontic appliances. In some embodiments, a system for providing data files associated with orthodontic appliances comprises a database, wherein the database stores the data files associated with the orthodontic appliances and a control circuit, wherein the control circuit is communicatively coupled to the database, a user device, and a printer, wherein the control circuit is configured to receive, from the user device, an indication of a selected orthodontic device, retrieve, based on the indication of the selected orthodontic device from the database, one of the data files associated with the orthodontic appliances, wherein the one of the data files associated with the orthodontic appliances corresponds to the selected orthodontic appliance, and transmit, to the printer, the one of the data files associated with the orthodontic appliances.

24 Claims, 20 Drawing Sheets

(51) Int. Cl.
*B33Y 80/00* (2015.01)
*A61C 13/00* (2006.01)
*B33Y 50/00* (2015.01)
*B33Y 70/00* (2020.01)

(52) U.S. Cl.
CPC ......... *A61C 2007/004* (2013.01); *B33Y 50/00* (2014.12); *B33Y 70/00* (2014.12); *B33Y 80/00* (2014.12)

(58) Field of Classification Search
USPC ....................................................... 345/419
See application file for complete search history.

(56) References Cited

U.S. PATENT DOCUMENTS

| | | | |
|---|---|---|---|
| 6,206,695 B1 | 3/2001 | Wong | |
| 7,648,360 B2 | 1/2010 | Kuo | |
| 7,940,258 B2 | 5/2011 | Stark | |
| 10,136,966 B2 | 11/2018 | Reybrouck | |
| 10,179,035 B2 | 1/2019 | Shivapuja | |
| 10,314,673 B2 | 6/2019 | Schulhof | |
| 2002/0064759 A1* | 5/2002 | Durbin | A61C 9/00 433/213 |
| 2004/0259049 A1 | 12/2004 | Kopelman | |
| 2007/0168152 A1 | 7/2007 | Matov et al. | |
| 2013/0081271 A1 | 4/2013 | Farzin-Nia | |
| 2014/0277659 A1* | 9/2014 | Kumar | G05B 19/4097 700/117 |
| 2017/0079747 A1 | 3/2017 | Graf | |
| 2018/0235730 A1 | 8/2018 | Djamchidi | |
| 2018/0314235 A1* | 11/2018 | Mirabella | B33Y 50/02 |
| 2020/0123383 A1* | 4/2020 | Wallin | C08L 83/08 |
| 2020/0275992 A1 | 9/2020 | Shannon et al. | |

\* cited by examiner

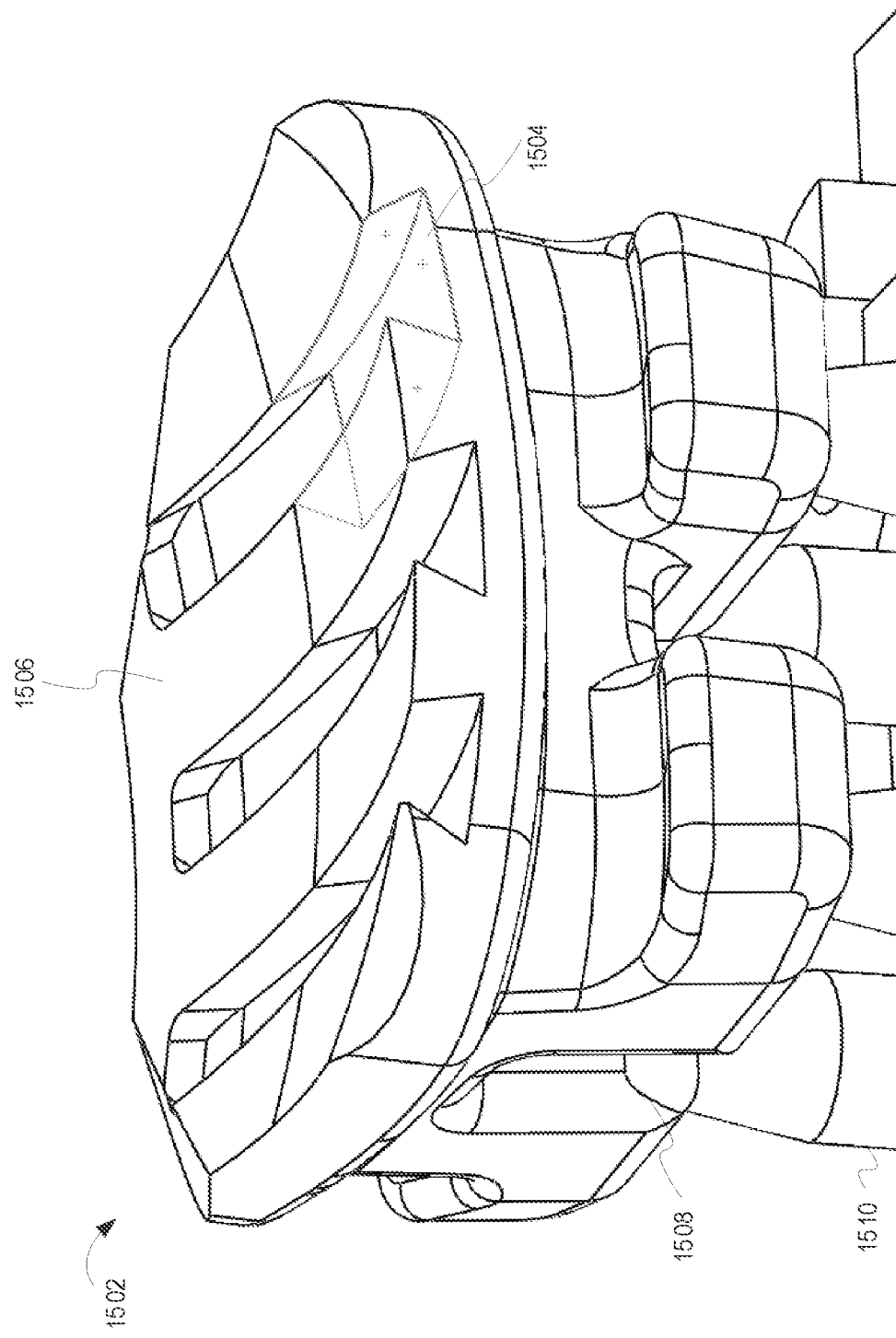

ized to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

SYSTEMS AND METHODS FOR MANUFACTURE OF ORTHODONTIC APPLIANCES

CROSS-REFERENCE TO RELATED APPLICATION

This application claims the benefit of U.S. Provisional Application No. 62/931,679, filed Nov. 6, 2019, which is incorporated by reference in its entirety herein.

TECHNICAL FIELD

This invention relates generally to orthodontics and, more specifically, the manufacture of orthodontic appliances

BACKGROUND

Orthodontic clinicians seek to correct malocclusions by use of many different devices, such as braces, retainers, pallet expanders, positioners, etc. Braces, one of the most commonly used appliances, include brackets, archwires, and ligatures. The brackets are affixed to a patient's teeth and the archwire passes through slots in the brackets designed to receive the archwire. The ligatures secure the archwire within the slots. Because no two patients have identical malocclusions or facial geometries, the prescription for each patient's braces must be selected by the clinician. A prescription for braces typically includes specifically selected brackets, archwires, and ligatures. Accordingly, many clinicians attempt to keep a variety of orthodontic appliances on-hand so as to be able to promptly treat patients. Unfortunately, doing so can be cost prohibitive. For example, a large practice may have an orthodontic bracket inventory costing over $50,000. Not only does this bracket inventory represent a large overhead for clinicians, it can prevent smaller practices from being able to do business. Consequently, a need exists for systems, methods, and apparatuses that minimize the need for clinicians to stock a large number of orthodontic appliances to treat patients.

BRIEF DESCRIPTION OF THE DRAWINGS

Disclosed herein are embodiments of systems, apparatuses, and methods pertaining to providing data files associated with orthodontic appliances. This description includes drawings, wherein:

FIG. 15 depicts a bracket 1502 including a dovetail 1504 through a bonding surface 1506 of the bracket 1502, according to some embodiments;

Figure 1:
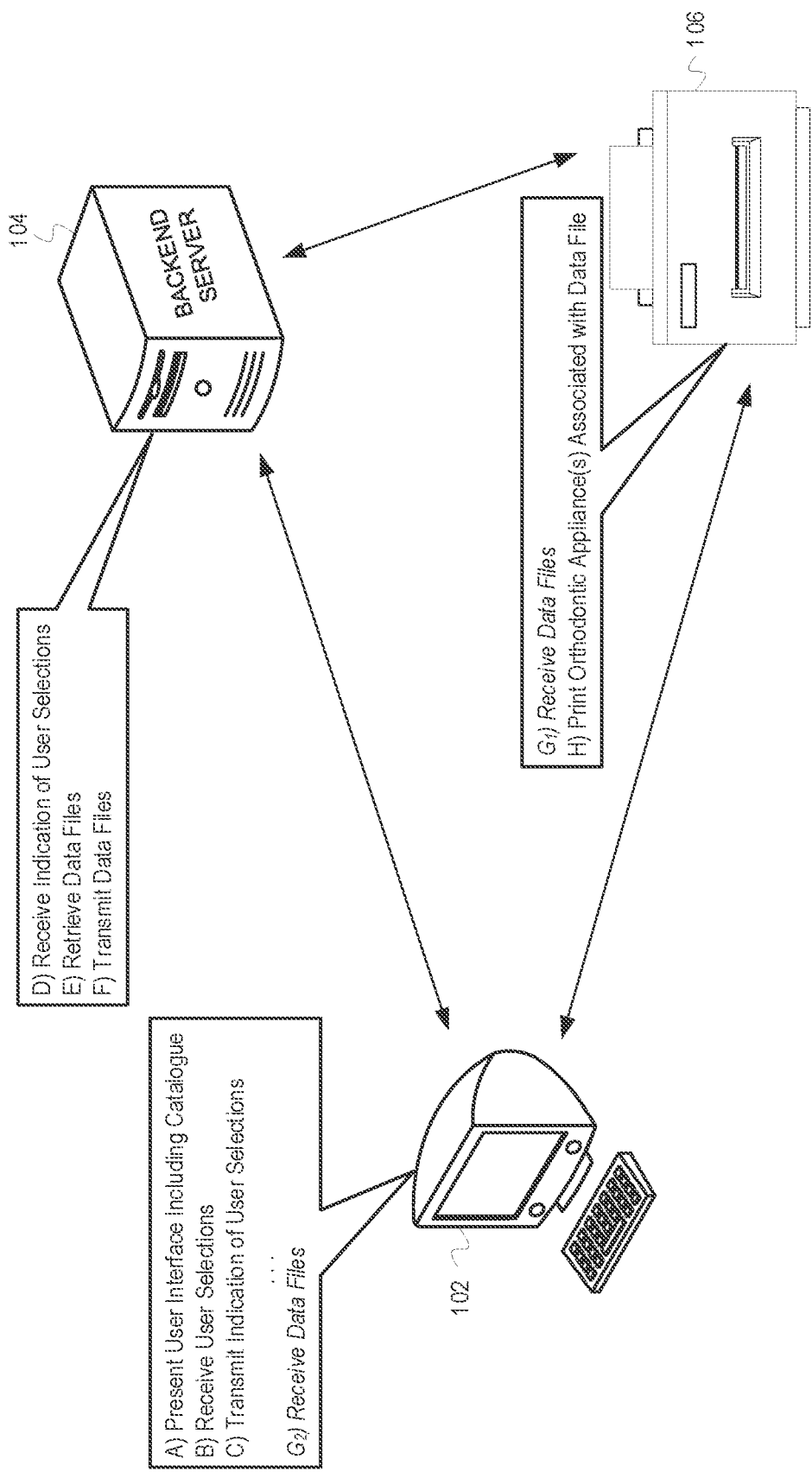
FIG. 1 is a diagram depicting operations between a user device 102, a backend server 104, and a printer 106 to additively manufacture an orthodontic appliance, according to some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses, and methods are provided herein useful to providing data files associated with orthodontic appliances. In some embodiments, a system for providing data files associated with orthodontic appliances comprises a database, wherein the database stores the data files associated with the orthodontic appliances and a control circuit, wherein the control circuit is communicatively coupled to the database, a user device, and a printer, wherein the control circuit is configured to receive, from the user device, an indication of a selected orthodontic device, retrieve, based on the indication of the selected orthodontic device from the database, one of the data files associated with the orthodontic appliances, wherein the one of the data files associated with the orthodontic appliances corresponds to the selected orthodontic appliance, and transmit, to the printer, the one of the data files associated with the orthodontic appliances.

As previously discussed, because no two patients have identical dental or facial structures, many orthodontic appliances are specially designed or selected for each patient. While some orthodontic appliances are custom-molded for patients, such as clear aligners, other orthodontic appliances, such as brackets, come in a variety of prescriptions and are selected by the clinician based on the patient's dental and/or facial geometry. With regard to brackets, clinicians select from among the commercially available prescriptions to choose brackets for each of a patient's teeth. While the total number of commercially available brackets is quite large, a smaller subset of all brackets is used to treat the majority of patients. For example, though the total number of commercially available brackets numbers in the thousands, the majority of patients are treated using only about 20% of those brackets. Accordingly, orthodontic practices may try to keep all of these "common" brackets on hand so that patients can be analyzed and treated promptly (e.g., during the same day, week, etc.). While maintaining such a large inventory may be feasible for large practices, maintaining, or building, such an inventory may be cost prohibitive for small and/or new practices. Additionally, even if a practice is capable of maintaining such an inventory, it is likely not cost effective.

Described herein are systems, methods, and apparatuses that seek to overcome this problem by allowing clinicians to quickly and affordably manufacture orthodontic appliances, such as brackets. In one embodiment, clinicians are provided with data files (e.g., computer-aided design files (CAD), such as .stl files). The clinicians then manufacture orthodontic appliances based on the data files with additive manufacturing. As one example, a clinician can select a bracket that he or she would like to use to treat a patient. The system provides a data file associated with the bracket to the clinician. The clinician then, using a 3D printer, manufactures the bracket in his or her office. This manufacturing-on-demand eliminates, or at least reduces, the number of brackets that a clinician must have on hand to promptly treat patients. Not only does this allow clinicians to promptly treat patients, but it also reduces costs for the clinician and thus the patient. The discussion of FIG. 1 provides an overview of such a system.

FIG. 1 is a diagram depicting example operations between a user device 102, a backend server 104, and a printer 106 to additively manufacture an orthodontic appliance, according to some embodiments. The example operations depicted in FIG. 1 include operations amongst the components of FIG. 1. FIG. 1 depicts operations at stages A-H. The stages are examples and are not necessarily discrete occurrences over time (e.g., the operations of different stages may overlap). Additionally, FIG. 1 is an overview of example operations.

At stage A, the user device 102 presents a user interface to the user. The user device 102 is, for example, a computing device (e.g., a desktop or laptop computer, tablet, smart- phone, etc.). The user interface includes a catalogue. The catalogue includes orthodontic appliances that are available. For example, the catalogue can include all orthodontic appliances that can be additively manufactured. In one embodiment, the catalogue is much like a traditional catalogue including orthodontic appliances for purchase. That is, the user can browse the available orthodontic appliances and select orthodontic appliances. The catalogue can include orthodontic appliances that are directly bonded (i.e. direct-bond orthodontic appliances) and/or removable orthodontic appliances (i.e., orthodontic appliances that are not affixed to the patient in a semi-permanent nature). For example, directly bonded orthodontic appliances can include brackets, buccal tubes, buttons, class II correctors, etc. and removable orthodontic appliances can include aligners, removable class II correctors, expanders, retainers, positioners, etc.

At stage B, the user device 102 receives user selections. The user selections can include selections of orthodontic devices. Additionally, in some embodiments, the user can make selections to modify the orthodontic appliances. In such embodiments, the catalogue can include a number of base orthodontic appliances (e.g., an orthodontic appliance of each type with default parameters). For example, the base orthodontic appliance can be a mini molar tube having default parameters or specifications (e.g., the mini molar tube can have an M-D width of 0.115", O-G height of 0.115 inches, Tip of zero degrees, Torque of 14 degrees, Offset of 7 degrees, Archwire Slot Width of 0.022", and In/Out of 0.033"). The user can then modify the mini molar tube by altering a slot width, a tip angulation, a tongue angulation, an offset angulation, a mesial-distal width, an occlusal-gingival height, an in-out height, a mesial-distal base radius, an occlusal-gingival base radius, a type of hook, a presence of a hook, a location of a hook, etc. of the mini molar tube. The modifications can be selections based on a discrete scale (e.g., the archwire slot can vary from 0.01" to 0.025" in 0.001" increments, the bracket can either include or not include a mesial hook, etc.) and/or be virtually infinitely adjustable. The user can select a single bracket, a group of brackets (e.g., a set of brackets for one patient's mouth), a pack of brackets (e.g., commonly used brackets to store in inventory), etc.).

At stage C, the user device 102 transmits an indication of the user selections to a backend server 104. For example, if the user selects 28 brackets (i.e., a group of brackets for a single patient's mouth), the user device 102 transmits an indication of each of the brackets selects by the user.

At stage D, the backend server 104 receives the indication of the user selections. The backend server 104 can be of any suitable type, and is generally responsible for processing the user selections, retrieving data files based on the user selections, and transmitting the data files. In some embodiments, the system can operate in a thin client manner. In such embodiments, the user device 102 can access the catalogue via the backend server 104. Additionally, or alternatively, some of the processing can be performed on the user device 102. For example, in some embodiments, the user device 102 may store a copy of the catalogue and present the catalogue to the user, as well as allow the user to make selections from the catalogue, via an application executing on the user device 102.

At stage E, the backend server 104 retrieves the data files. The data files are associated with orthodontic appliances. For example, the data files can be CAD files, such as .cad, .fbx. stl, .form, etc. files, and include engineering drawings for the orthodontic appliances. The engineering drawings of the orthodontic appliances are suitable for use in manufacturing the orthodontic appliances. That is, the data files include information sufficient to additively manufacture an orthodontic appliance. The backend server 104 retrieves the data files that are associated with the user's selections. For example, if the user selects a Lower Anterior bracket with an M-D width of 0.115", O-G height of 0.151 inches, Tip of zero degrees, Torque of −6 degrees, Offset of 0 degrees, Archwire Slot Width of 0.022", In/Out of 0.045", No Mesial Hook, No Gingival Hook, O-G Base Radius of 0.625, and M-D Base Radius of 0.375", the backend server 104 retrieves the data file associated with a Lower Anterior bracket anterior bracket having these parameters. In some embodiments, the data files are generated, and stored in a database, before the time at which they are requested. That is, the data files are pre-generated and need not be created at the time of retrieval. In such embodiments, data files may be created for each permutation of each bracket and stored in a database for quick and easy retrieval. Alternatively, in some embodiments, at least some of the data files are not pre-generated. For example, in some embodiments, only data files for the base brackets may be pre-generated. In such embodiments, the data files for the base brackets are modified to when a user makes modifications to the base bracket.

At stage F, the backend server 104 transmits the data files. The backend server 104 can transmit the data files to the user device 102 and/or the printer 106, dependent upon the environment. For example, in one embodiment, the backend server 104 transmits the data files to the user device 102 (stage $G_2$) and the user device 102 transmits the data files to the printer 106 for printing. Alternatively, the backend server 104 transmits the data files directly to the printer 106 (stage $G_1$) for printing. In either case, the data files may be secured so that orthodontic appliances based on the data files may only be manufactured once. That is, the user may purchase a number of prints of each data file, as opposed to purchasing the data file. For example, if the user selects only a single bracket and one copy of the single bracket, in such embodiments the user is only able to print the single bracket once. Such control can be achieved by any suitable means, such as single-use encryption, transmission of data files directly to the printer 106, using specific file formats (e.g., file formats that are difficult to manipulate, proprietary, etc.), etc. In some embodiments, the user can purchase a subscription (e.g., an unlimited number of prints for a month, a specified number of prints for a week, etc.).

At stage H, the printer 106 prints the orthodontic appliances associated with the data files. Though this description refers to a printer 106 printing an orthodontic appliance, embodiments are not so limited and the term "printing" is used herein to generally refer to any suitable additive manufacturing process.

Figure 2:
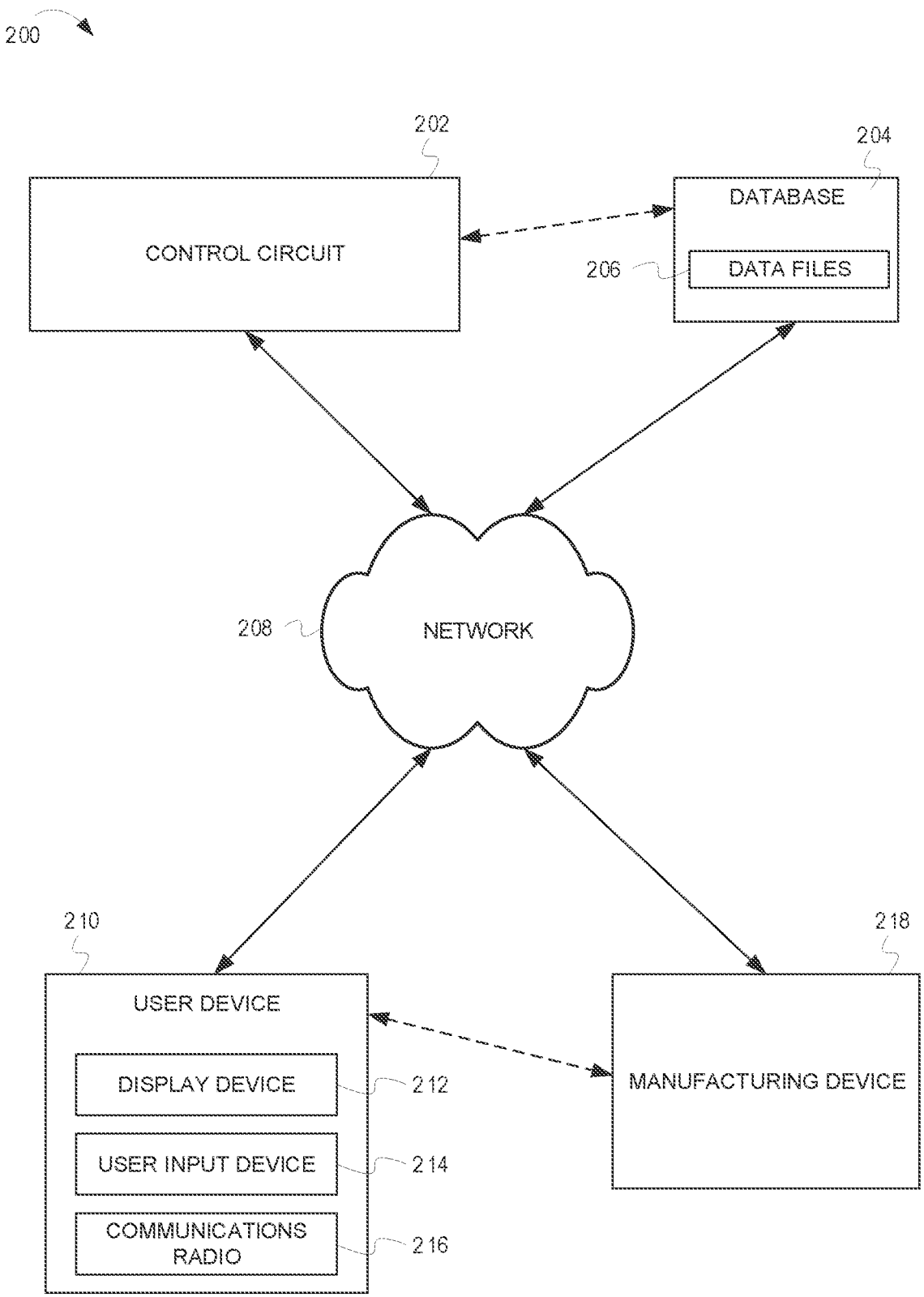
FIG. 2 is a block diagram of a system 200 for providing data files associated with orthodontic appliances, according to some embodiments.

While the discussion of FIG. 1 provides an overview of operations performed by a system to additively manufacture orthodontic appliances, the discussion of FIG. 2 provides additional detail regarding such a system.

FIG. 2 is a block diagram of a system 200 for providing data files associated with orthodontic appliances, according to some embodiments. The system 200 includes a control circuit 202, a database 204, a user device 210, and a manufacturing device 218. One or more of the control circuit 202, the database 204, the user device 210, and the manufacturing device 218 are communicatively coupled via a network 208. The network 208 can include a local area network (LAN) and/or wide area network (WAN), such as the internet. Accordingly, the network 208 can include wired and/or wireless links.

The user device 210 can be any suitable type of computing device (e.g., a desktop or laptop computer, smartphone, tablet, etc.). The user device 210 includes a display device 212. The display device 212 is configured to present a catalogue to a user. The catalogue includes orthodontic appliances that the user can obtain via the system 200. For example, the catalogue can include all orthodontic devices that the user can purchase and/or manufacture via the manufacturing device 218. The user interacts with the catalogue via a user input device 214. The user can interact with the catalogue by navigating the catalogue, making selections from the catalogue, modifying orthodontic appliances included in the catalogue, etc. Accordingly, the user input device 214 can be of any suitable type, such as a mouse, keyboard, trackpad, touchscreen, etc. The user device 210 also includes a communications radio 216. The communications radio 216 transmits and receives information for the user device 210. For example, in the case of a smartphone, the communications radio 216 can be a cellular radio operating in accordance with the 4G LTE standard. Once a user has made a selection of an orthodontic appliance, the user device 210, via the communications radio 216 and the network 208, transmits an indication of the selection to the control circuit 202.

The control circuit 202 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. The control circuit 202 is configured (for example, by using corresponding programming as will be well understood by those skilled in the art) to carry out one or more of the steps, actions, and/or functions described herein.

By one optional approach the control circuit 202 operably couples to a memory. The memory may be integral to the control circuit 202 or can be physically discrete (in whole or in part) from the control circuit 202 as desired. This memory can also be local with respect to the control circuit 202 (where, for example, both share a common circuit board, chassis, power supply, and/or housing) or can be partially or wholly remote with respect to the control circuit 202 (where, for example, the memory is physically located in another facility, metropolitan area, or even country as compared to the control circuit 202).

This memory can serve, for example, to non-transitorily store the computer instructions that, when executed by the control circuit 202, cause the control circuit 202 to behave as described herein. As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).

The control circuit may be remote from the user device 210 and/or the manufacturing device 218. For example, the user device 210 and the manufacturing device 218 may be located in a clinician's office (e.g., the user's office) whereas the control circuit 202, and possibly the database 204, are cloud-based. The control circuit 202 generally operates to retrieve data files 206 based on the user's selection of orthodontic appliances. The control circuit 202 retrieves the data files 206 from the database 204. The database 204 is configured to store the data files 206. The data files 206 are associated with orthodontic appliances. The data files 206 are CAD files from which the orthodontic devices can be manufactured. The database 204 stores a data file for each of the orthodontic appliances included in the catalogue. In one embodiment, the database 204 stores a data file for all possible permutations of each orthodontic appliance (e.g., every possible modification and/or combination or modifications for each orthodontic appliance). The control circuit 202 receives the indication of the orthodontic appliance and retrieves a data file based on the indication of the orthodontic appliance.

It should be noted that the indication of the orthodontic appliance may include more than one orthodontic appliance. For example, the indication of the orthodontic appliance can include multiple orthodontic appliances, such as full set of brackets for a patient. Accordingly, the data file can be a file including instructions and/or specifications for multiple orthodontic appliances. For example, the data file may include multiple data files and/or multiple specifications for a number of brackets.

After retrieving the data file, the control circuit 202 transmits the data file. In some embodiments, the control circuit 202 encrypts or otherwise protects the data file before transmission. The control circuit 202 can encrypt or otherwise protect the data file before transmission to prevent those other than the user from accessing the data file. Additionally, in some embodiments, the control circuit 202 can encrypt or otherwise protect the data file to control the user's access to the data file. For example, in some embodiments, the system is set up such that user's pay on a per manufacture or per print basis. That is, the user does not purchase, and may not later have access to, the data file. Rather, the user purchases access to print or otherwise manufacture an orthodontic appliance based on the data file once (or other specified number of times).

Dependent upon the embodiment, the control circuit 202 transmits the data file to the user device 210, the manufacturing device 218, or a third-party device (e.g., a laboratory capable of manufacturing the orthodontic appliance for the user). To whom, or to what device, the data file is transmitted may also aid in achieving access control. For example, in one embodiment, the control circuit 202 transmits the data file directly to the manufacturing device 218. Because the data file is not transmitted to the user device 210, the data file may not be easily accessible by the user device 210. Further, if an entity that controls the control circuit 202 controls the manufacturing device 218, access may to files received by the manufacturing device 218 may be further limited. In some embodiments, the control circuit 202 transmits the data files to the user device 210. In such embodiments, the user device 210 transmits, via the communications radio (e.g., over a universal serial bus (USB) connection, wireless connection based on the 802.11 standard, etc.), the data files to the manufacturing device 218.

The manufacturing device 218 additively manufacturers the orthodontic appliance(s) based on the data file. The manufacturing device 218 can be of any suitable type, such as a 3D printer. The manufacturing device 218 can be local to, or remote from, one or more of the control circuit 202 and the user device 210. For example, in one embodiment, the user device 210 and the manufacturing device 218 are located in the user's office (i.e., the user device 210 and the manufacturing device 218 are local to one another). Alternatively, the manufacturing device 218 may be located in a laboratory or some other facility that manufactures orthodontic appliances for the user.

Figure 3:
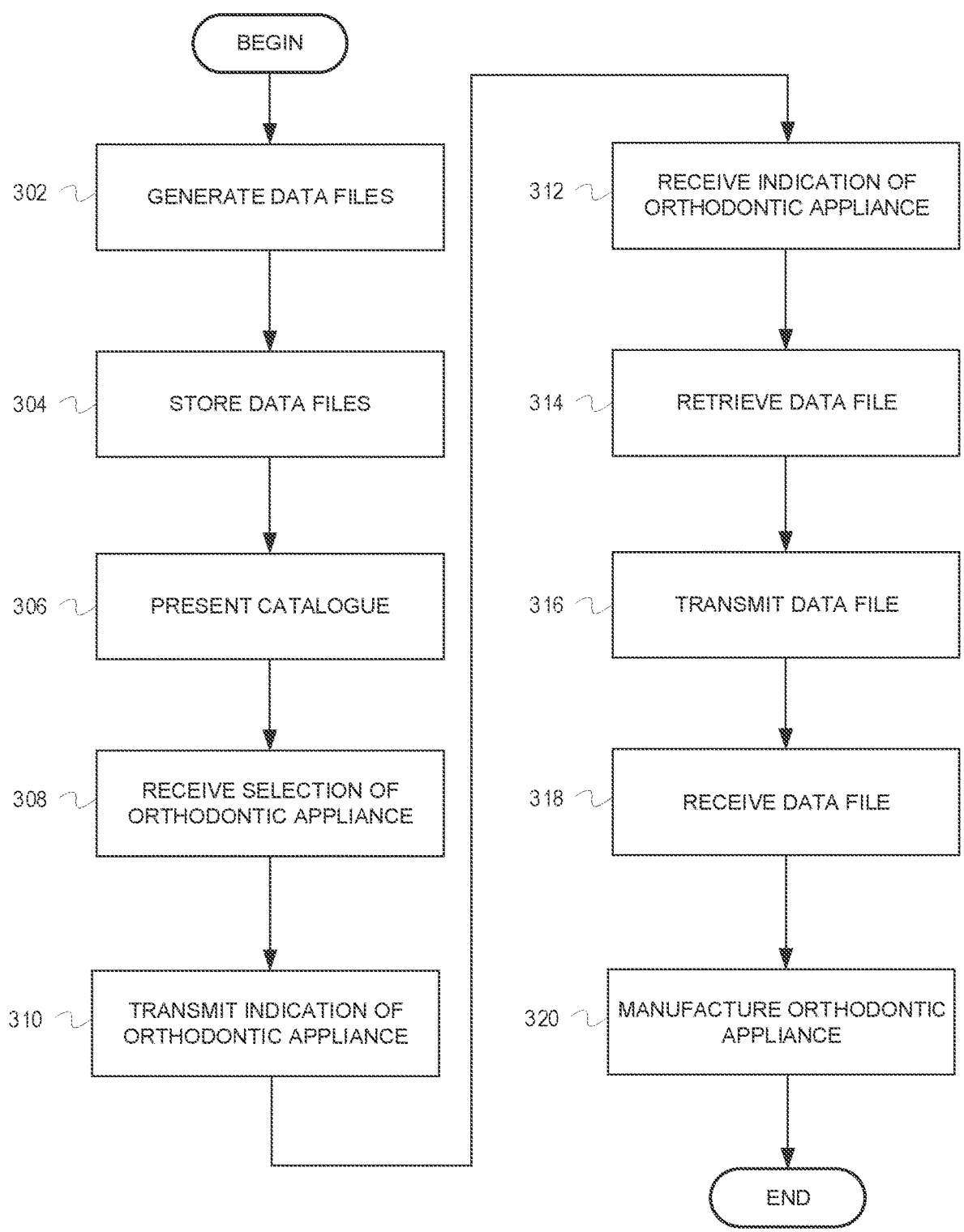
FIG. 3 is a flow chart including example operations for providing data files associated with orthodontic appliances, according to some embodiments.

While the discussion of FIG. 2 provides additional detail regarding a system for providing data files associated with orthodontic appliances, the discussion of FIG. 3 describes example operations of such a system.

FIG. 3 is a flow chart including example operations for providing data files associated with orthodontic appliances, according to some embodiments. The flow begins at block 302.

At block 302, data files are generated. For example, a human user and/or computer program can generate the data files. The data files are associated with orthodontic appliances. The data files are associated with orthodontic appliances such that the data files can be used to manufacture or otherwise produce orthodontic appliances based on the data files. In one embodiment, the data files are CAD files. The data files can be generated before, or at the time of, retrieval. The flow continues at block 304.

At block 304, the data files are stored. For example, a database can store the data files. The database can be of any suitable type and store the data files in any suitable manner. For example, the database can be a relational database, a NoSQL database, etc. The database stores the data files after they are generated. The flow continues at block 306.

At block 306, a catalogue is presented. For example, a user device can present the catalogue to a user. The catalogue includes orthodontic appliances that the user can purchase or otherwise obtain. The user can browse the catalogue and make selections via the user device. The flow continues at block 308.

At block 308, selection of an orthodontic appliance is received. For example, the user device can receive a selection of an orthodontic appliance. The selection of the orthodontic appliance can indicate which orthodontic appliance the user would like to manufacture and, in some embodiments, can also indicate modifications to the orthodontic appliance. For example, the catalogue can include a number of base orthodontic appliances. At least some of the base orthodontic appliances are modifiable by the user. The user selection can include an indication of the modifications. The flow continues at block 310.

At block 310, an indication of the orthodontic appliance is transmitted. For example, the user device can transmit an indication of the orthodontic appliance via a network. The indication of the orthodontic appliance indicates which orthodontic appliance(s) the user has chosen as well as any modifications to the orthodontic appliance(s). The flow continues at block 312.

At block 312, the indication of the orthodontic appliance is received. For example, a control circuit can receive the indication of the orthodontic appliance. The flow continues at block 314.

At block 314, a data file is retrieved. For example, the control circuit can retrieve the data file from the database. The data file is associated with the orthodontic appliance. That is, the data file includes the instructions and/or parameters necessary to manufacture the orthodontic appliance that the user has selected. In some embodiments, the control circuit can encrypt or otherwise protect the data file. As one example, the control circuit can encode the data file with single use encryption. The flow continues at block 316.

At block 316, the data file is transmitted. For example, the control circuit can transmit the data file. The control circuit can transmit the data file to the user device and/or a manufacturing device. The flow continues at block 318.

At block 318, the data file is received. For example, the data file can be received by the user device and/or the manufacturing device. If the data file is received by the user device, the user device transmits the data file to the manufacturing device. The flow continues at block 320.

At block 320, the orthodontic appliance is manufactured. For example, the manufacturing device can manufacture the orthodontic appliance. The manufacturing device can be of any type suitable to additively manufacture the orthodontic appliance. For example, the manufacturing device can be a 3D printer.

While the discussion of FIGS. 1-3 provides detail regarding a system for providing data files associated with orthodontic appliances, the discussion of FIGS. 4-11 describe a user's interaction with such a system via a user interface.

Figure 4:
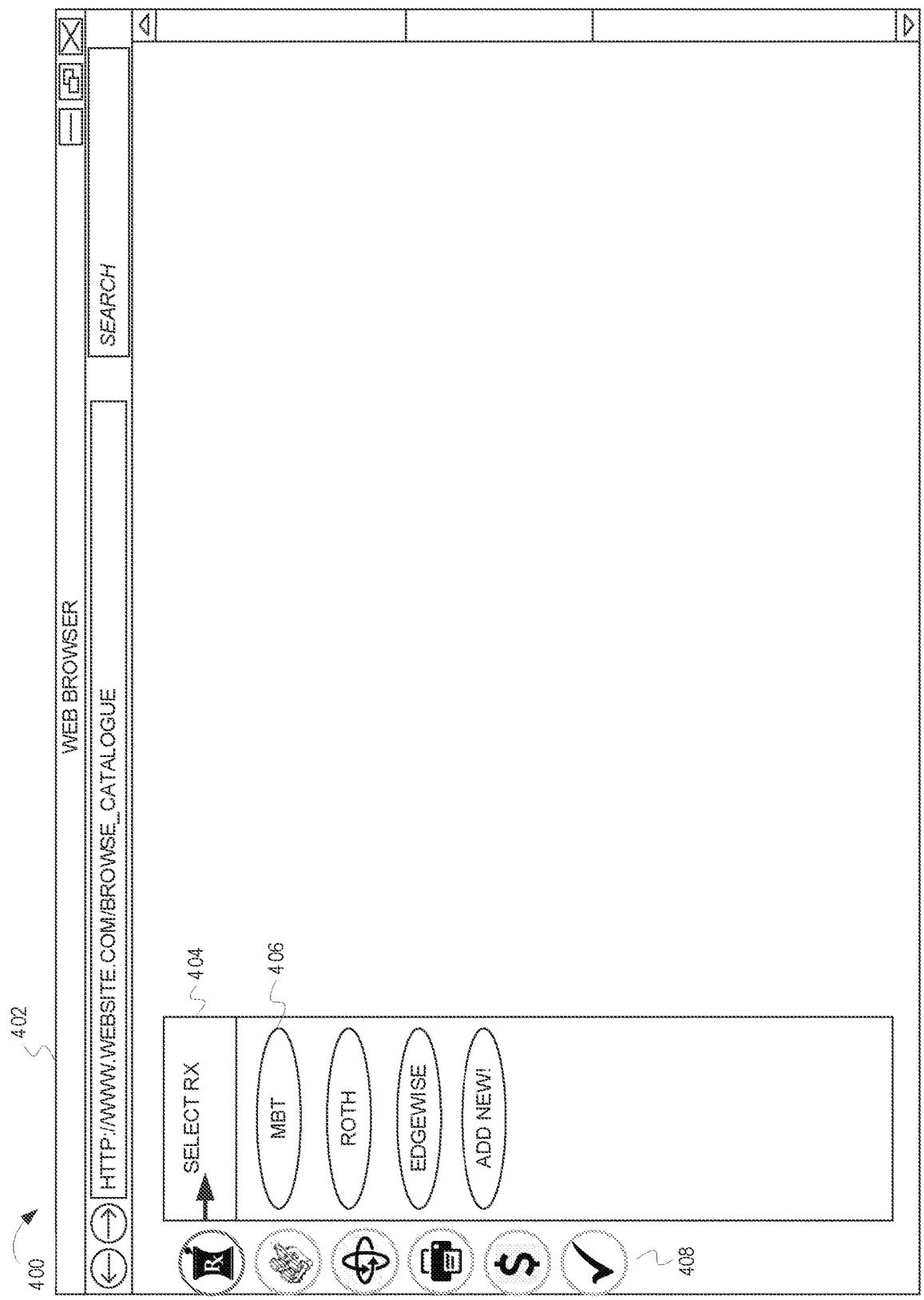
FIG. 4 depicts a user interface 402 for selecting orthodontic appliances, according to some embodiments.

FIG. 4 depicts a user interface 402 for selecting orthodontic appliances, according to some embodiments. In FIG. 4 (as well as FIGS. 5-11), the user interface 402 is being presented via a web browser 400. It should be noted that this is just one example. In some embodiments, a software application specific to the catalogue may execute on the user device. In such embodiments, the user interface may be presented via the software application. Whether the system operates as a thin client or a thick client, the general functionality remains this same. Consequently, the description provided in FIGS. 4-11, though directed to an example in which the system operates as a thin client, is applicable to thick client embodiments as well.

FIG. 4 depicts a root menu 408 of the user interface 402. The root menu 408 includes a number of selections. In FIG. 4, the user is on the first step, as indicated by user selection of a select prescription menu 404. Selection of the select prescription selection 404 causes the user interface 402 to present different prescription types 406 from which the user can select. In some embodiments, the prescription types 406 include standard prescriptions known in the art as well as the option to create a new prescription ("Add New!").

Figure 5:
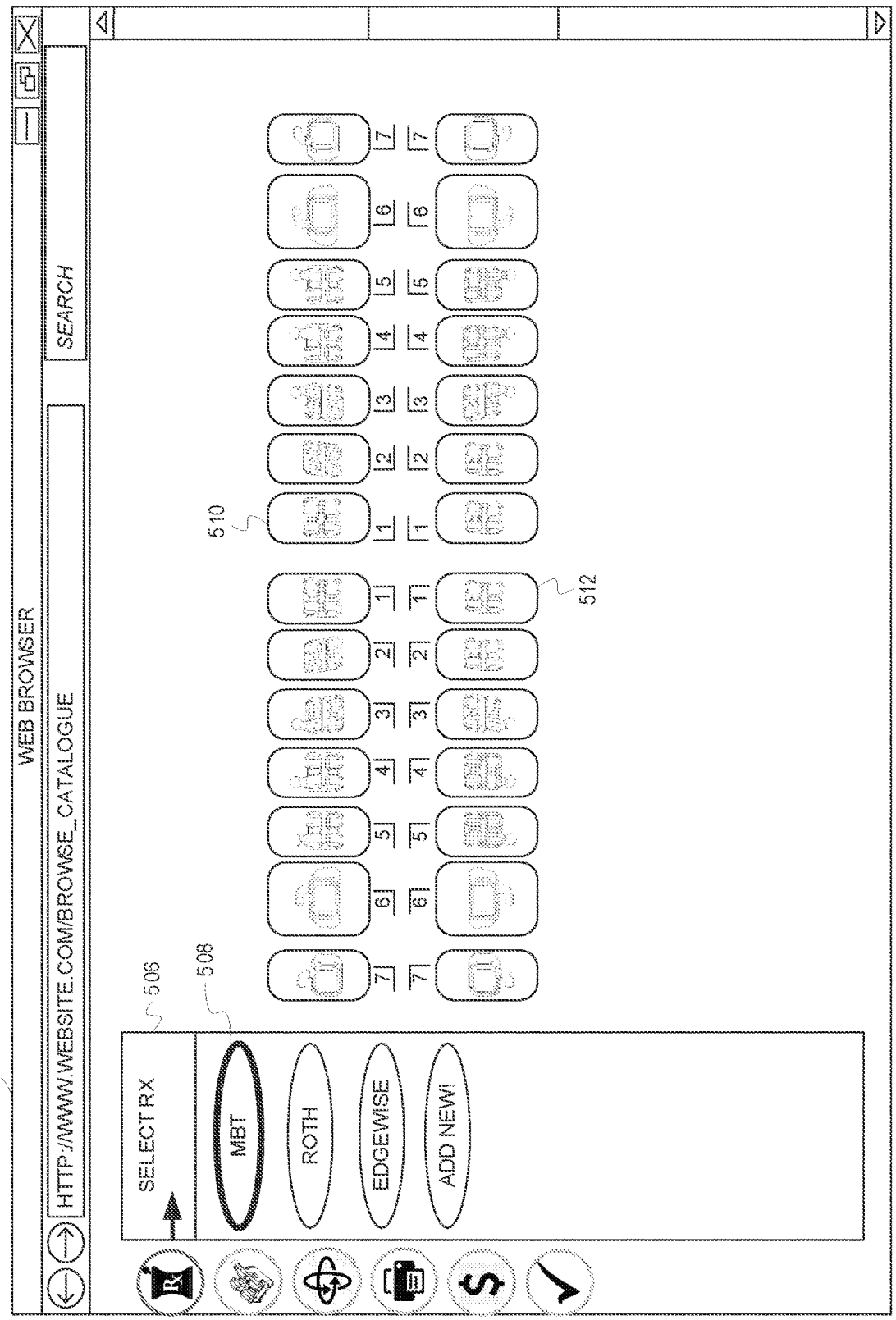
FIG. 5 depicts selection of a prescription type for an orthodontic appliance via a user interface 502 for selecting orthodontic appliances, according to some embodiments.

FIG. 5 depicts selection of a prescription type for an orthodontic appliance via a user interface 502 for selecting orthodontic appliances, according to some embodiments. As shown in FIG. 5, the user has selected the MBT 508 prescription type from a select prescription menu 506. Selection of the MBT 508 prescription type causes the user interface 502 to present orthodontic appliances for each of a patient's teeth, including a first set of brackets 510 for the top row of the patient's teeth and a second set of brackets 512 for the bottom row of the patient's teeth. In some embodiments, the brackets of the first set of brackets 510 and the second set of brackets 512 are automatically populated by upon selection of a prescription type. For example, the user interface can be prepopulated with common brackets, suggested brackets (e.g., based on a scan of the patient's mouth provided to the system), brackets previously selected by the user, etc.

Figure 6:
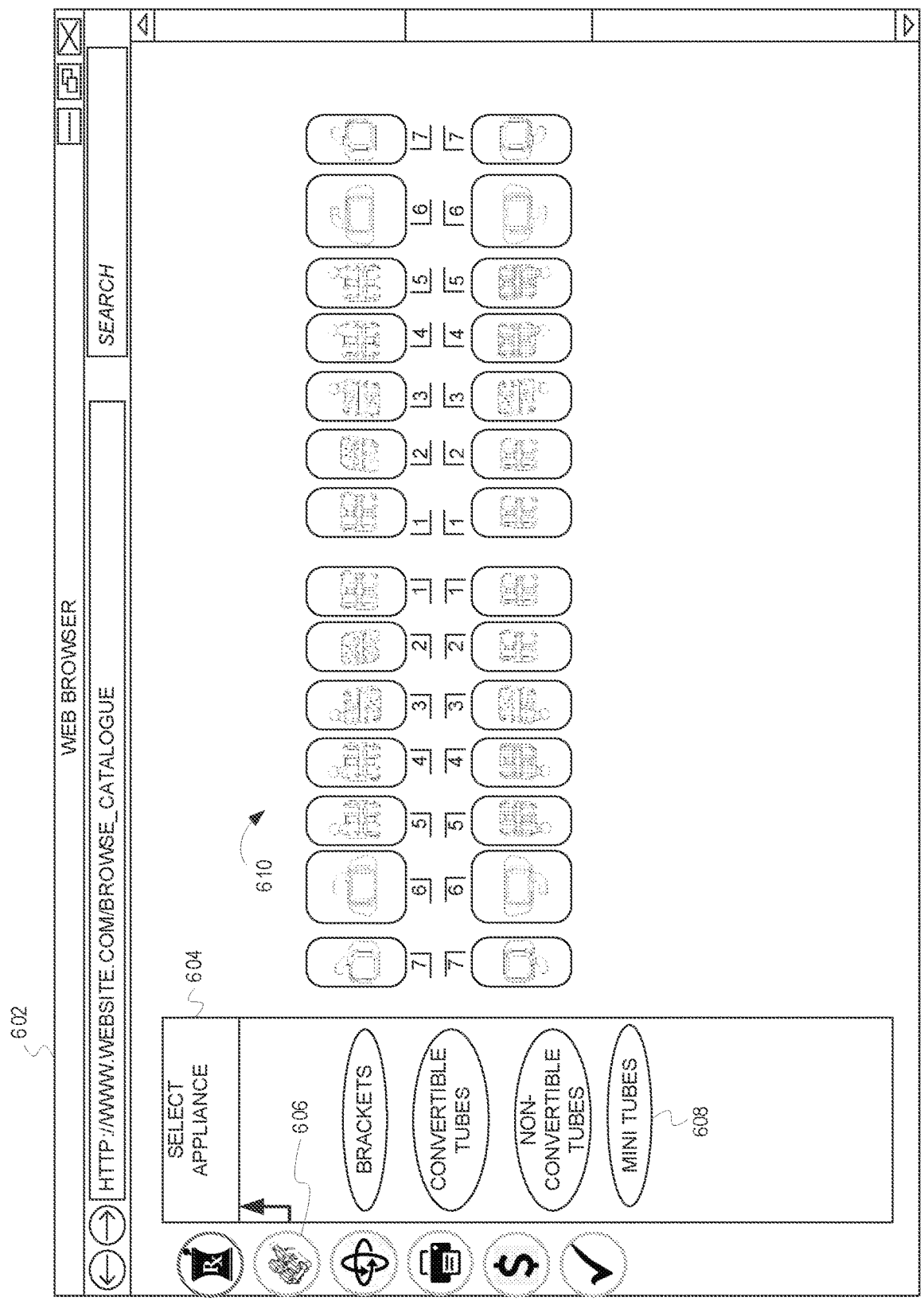
FIG. 6 depicts selection of a type of orthodontic appliance via a user interface 602 for selecting orthodontic appliances, according to some embodiments.

FIG. 6 depicts selection of a type of orthodontic appliance via a user interface 602 for selecting orthodontic appliances, according to some embodiments. As depicted in FIG. 6, the user has selected the orthodontic appliance type 606. Selection of the orthodontic appliance type 606 presents a menu 608 of different types of orthodontic appliances from which the user can select. At this stage, the user interface 602 presents a graphic 610 of each tooth and the orthodontic appliance, if any, selected for that tooth.

Figure 7:
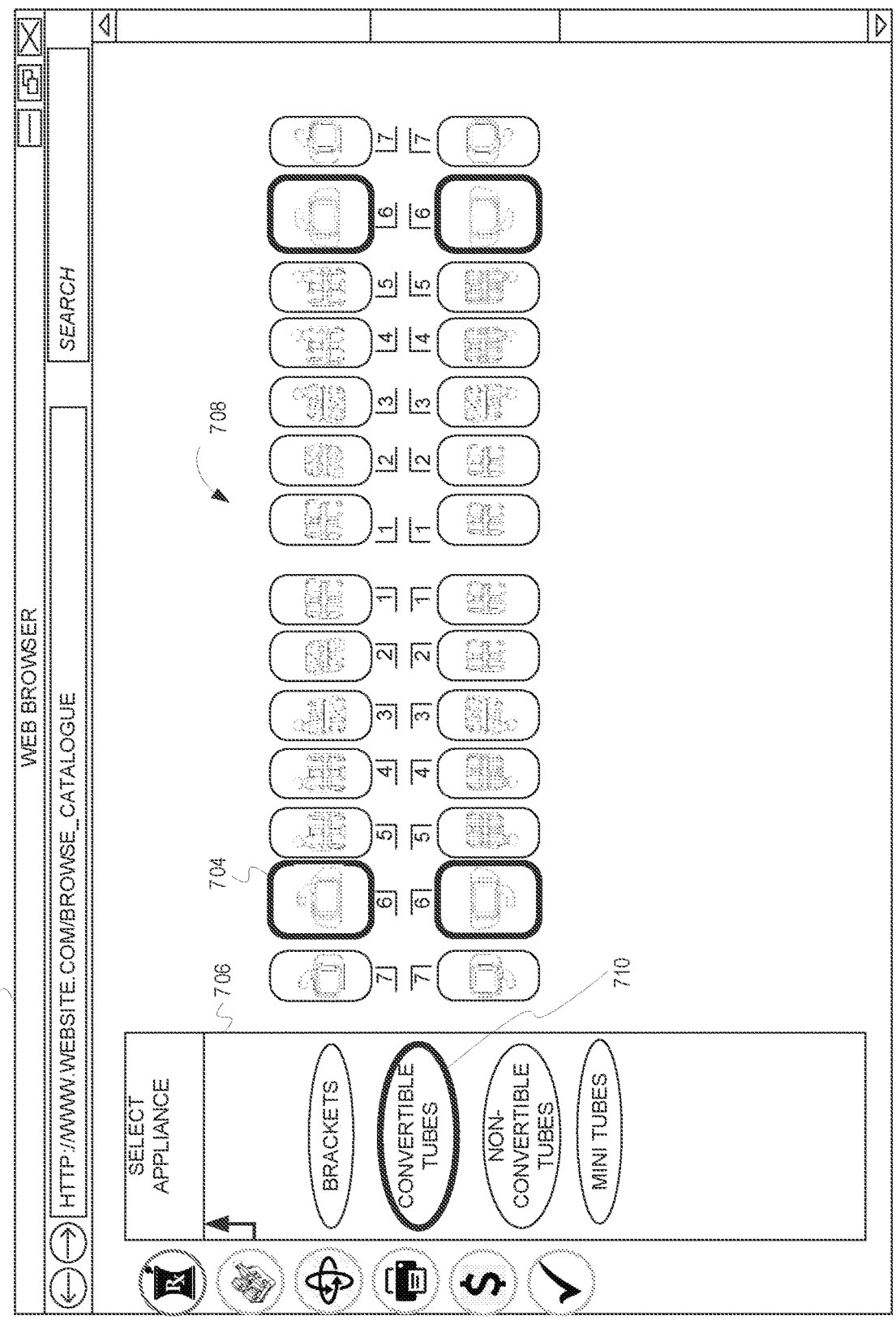
FIG. 7 depicts selection of a type of orthodontic appliance via a user interface 702 for selecting orthodontic appliances, according to some embodiments.

FIG. 7 depicts selection of a type of orthodontic appliance via a user interface 702 for selecting orthodontic appliances, according to some embodiments. In FIG. 7, the user has selected the convertible tube selection 710 from the menu 706 of different types of orthodontic appliances. The user has also selected teeth from the graphic 708 with which he or she would like to associate convertible tubes. As depicted in FIG. 7, the user has selected the upper first molars 704. The graphic 708 allows the user to visualize his or her selections as he or she develops the prescription for the patient.

Figure 8:
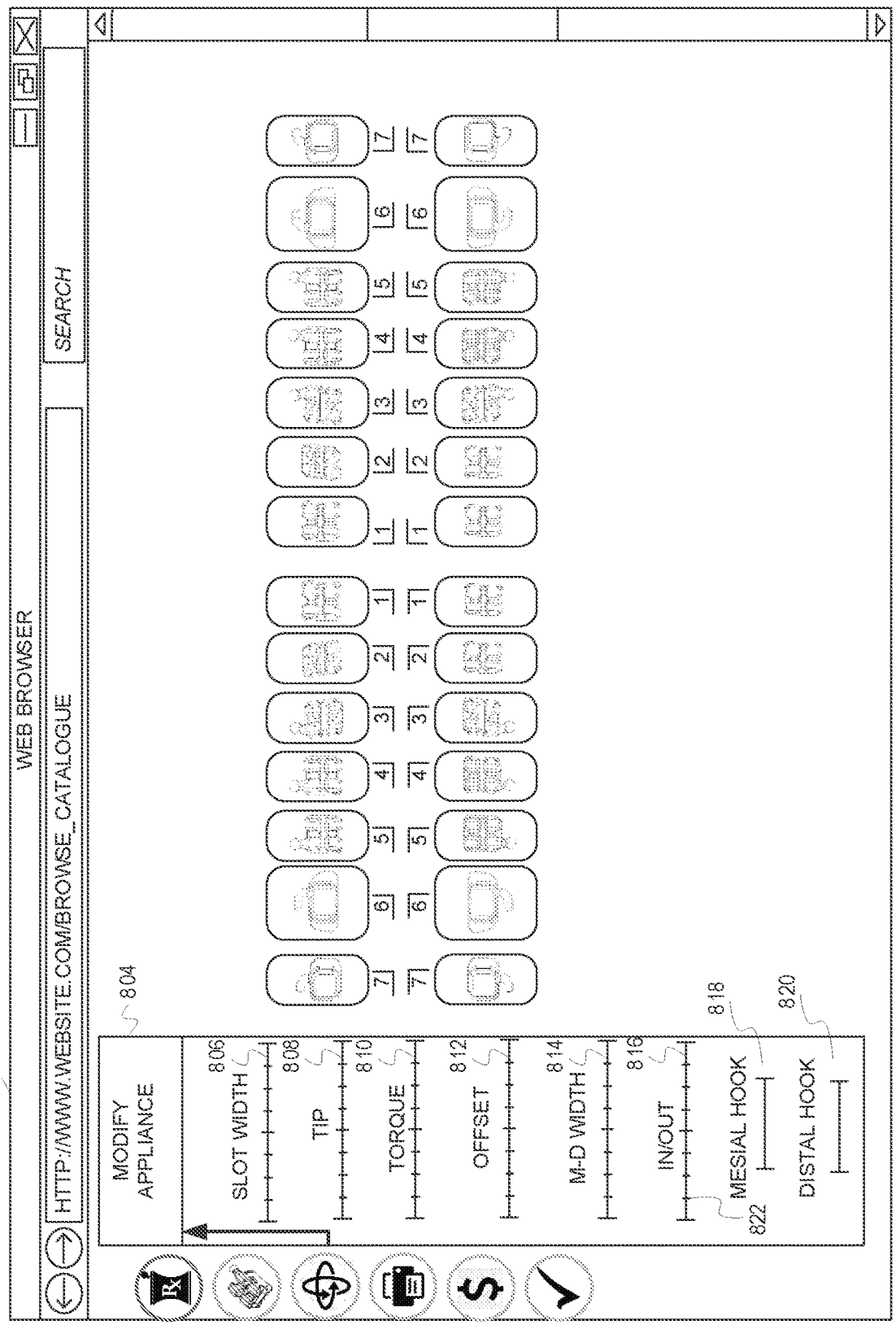
FIG. 8 depicts a modification menu 804 of a user interface 802 for selecting orthodontic appliances, according to some embodiments.

FIG. 8 depicts a modification menu 804 of a user interface 802 for selecting orthodontic appliances, according to some embodiments. As depicted in FIG. 8, the user has selected a modification menu 804. The modification menu 804 allows the user to make changes to the parameters of the orthodontic appliances. For example, as depicted in FIG. 8, the user can modify the slot width 806 of the orthodontic appliance, the tip 808 of the orthodontic appliance, the torque 810 of the orthodontic appliance, the offset 812 of the orthodontic appliance, the mesial-distal (M-D) width 814 of the orthodontic appliance, the in/out 816 of the orthodontic appliance, the presence of a mesial hook 818 on the orthodontic appliance, and the presence of a distal hook 820 on the orthodontic appliance. A greater number of, or fewer, modifications are possible as desired, and the modifications provided herein are simply examples of modifications that a user may wish to make.

As depicted in FIG. 8, each of the modifications includes an incremented bar 822. The user can adjust the modifications based on this incremented bar 822. The incremented bar 822 is incremented as suited for the modification. For example, the presence of a mesial hook is binary (i.e., either the orthodontic appliance will have or will not have a mesial hook) and thus the incremented bar 822 associated with the mesial hook modification has two increments.

Figure 9:
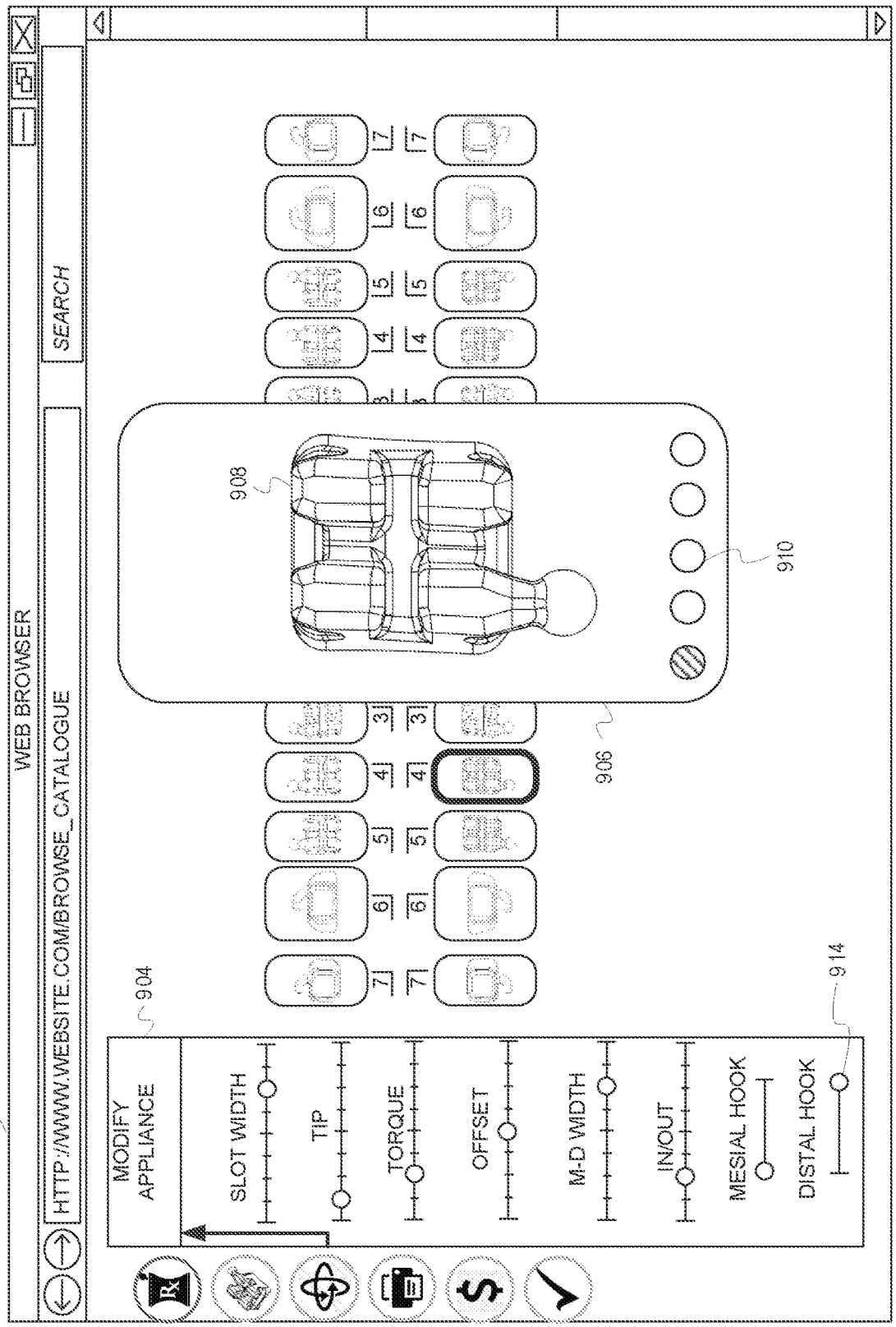
FIG. 9 depicts modification of an orthodontic appliance via selections of a modification menu 904 of a user interface 902 for selecting orthodontic appliances.

FIG. 9 depicts modification of an orthodontic appliance via selections of a modification menu 904 of a user interface 902 for selecting orthodontic appliances. As depicted in FIG. 9, the user has selected the lower right first bicuspid. Upon selection of a tooth, the user interface 902 presents an expanded view 906 of the orthodontic appliance for the selected tooth. Here, the user has selected a bracket 908 for the selected tooth. In the expanded view 906, the user can select from a number of views, as indicated by markers 910. The number of views can include front elevation, rear elevation, isometric, top, bottom, sectional, etc. views. Additionally, in some embodiments, one or more of the views can be dynamic. For example, in one or more of the views, the user may be able to manipulate a virtual representation of the bracket 908. As depicted in FIG. 9, the user has manipulated the incremented bars 914 to modify the bracket 908 as desired.

Figure 10:
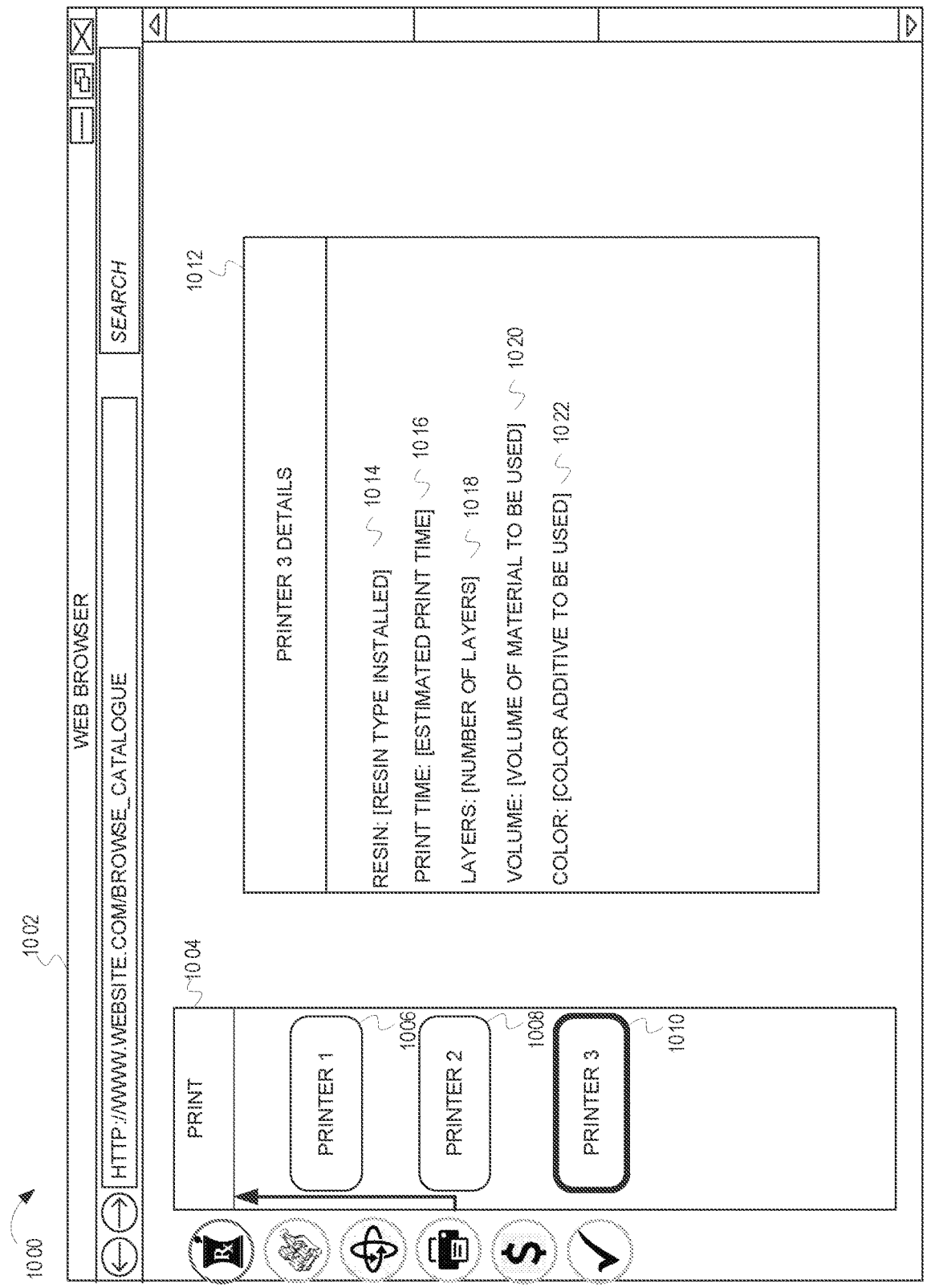
FIG. 10 depicts a print menu 1004 of a user interface 1002 for selecting orthodontic appliances, according to some embodiments.

FIG. 10 depicts a print menu 1004 of a user interface 1002 for selecting orthodontic appliances, according to some embodiments. In FIG. 10, the user has selected the print menu 1004. Selection of the print menu 1004 causes the user interface 1002 to present printers from which the user can select. In the example depicted in FIG. 10, the user can select from three printers: Printer 1 1006, Printer 2 1008, and Printer 3 1010. As depicted in FIG. 10, the user has selected Printer 3 1010. Selection of Printer 3 1010 causes the user interface 1002 to present a printer dialogue 1012 associated with Printer 3. The printer dialogue 1012 includes information about Printer 3 1010, such as the type of resin installed 1014, estimated print time 1016, number of layers 1018, volume of material to be used 1020, color additive to be used 1022, etc.

Figure 11:
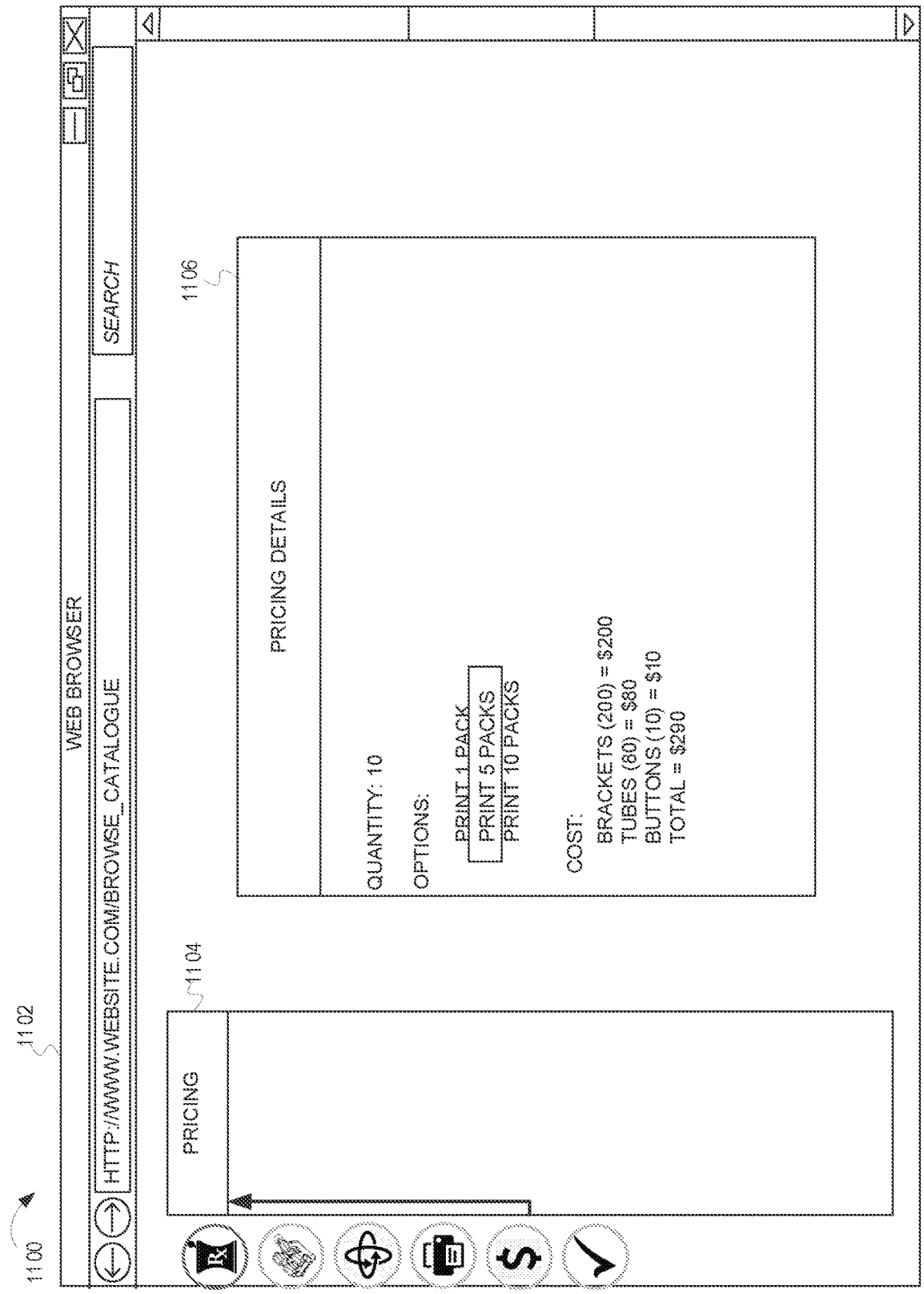
FIG. 11 depicts a pricing menu 1104 or a user interface 1102 for selecting orthodontic appliances, according to some embodiments.

FIG. 11 depicts a pricing menu 1104 or a user interface 1102 for selecting orthodontic appliances, according to some embodiments. Selection of the pricing menu 1104 causes the user interface 1102 to present a pricing details dialogue 1106. The pricing details dialogue 1106 presents pricing information for the user. For example, the pricing dialogue 1106 can include a description of the orthodontic appliances that the user would like to order, a cost associated with each of the orthodontic appliances that the user would like to order, total costs, etc.

While the discussion of FIGS. 4-11 provides additional detail regarding a user interface for selecting orthodontic appliances, the discussion of FIGS. 12 and 13 provide additional detail regarding manufacture of sets of orthodontic appliances.

Figure 12A:
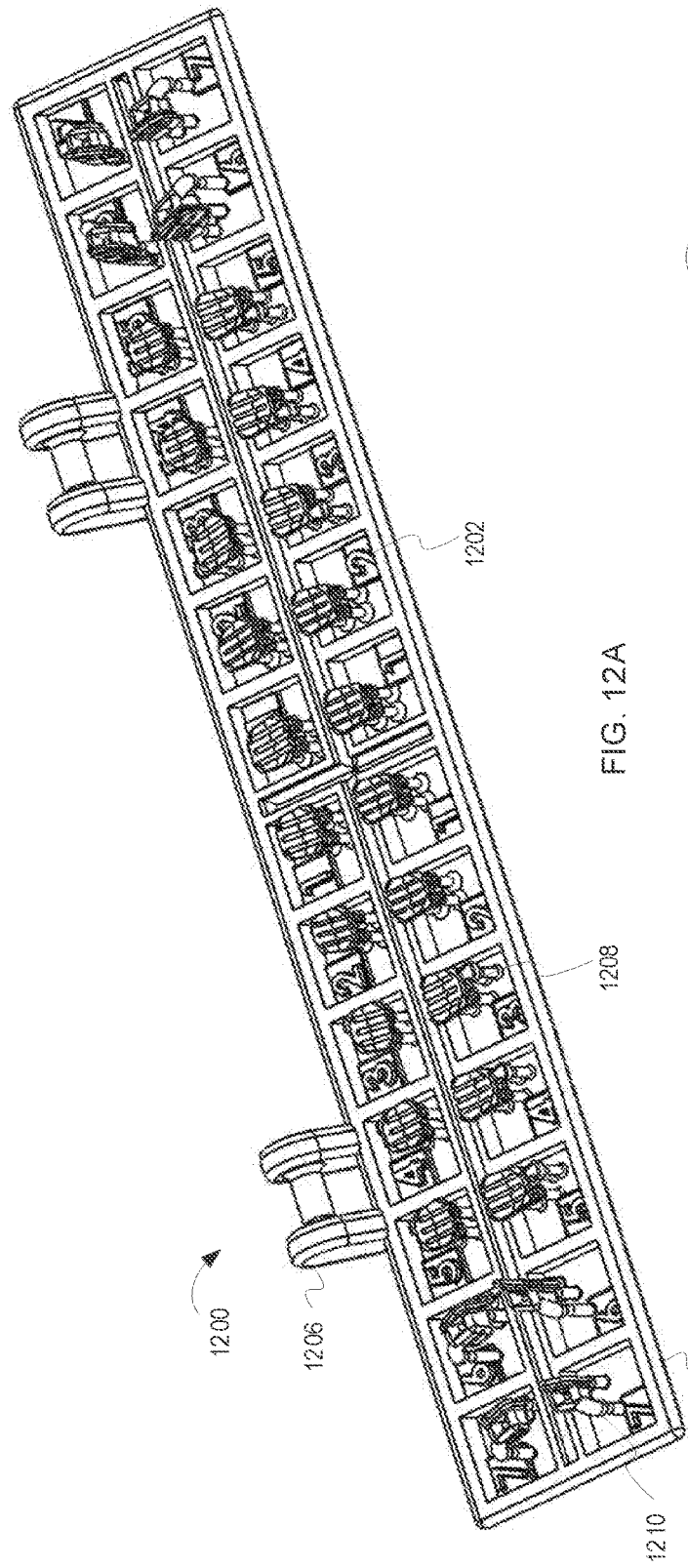
FIGS. 12A and 12B depict isometric and plan views, respectively, of base 1200 of a kit including orthodontic appliances, according to some embodiments.
Figure 12B:
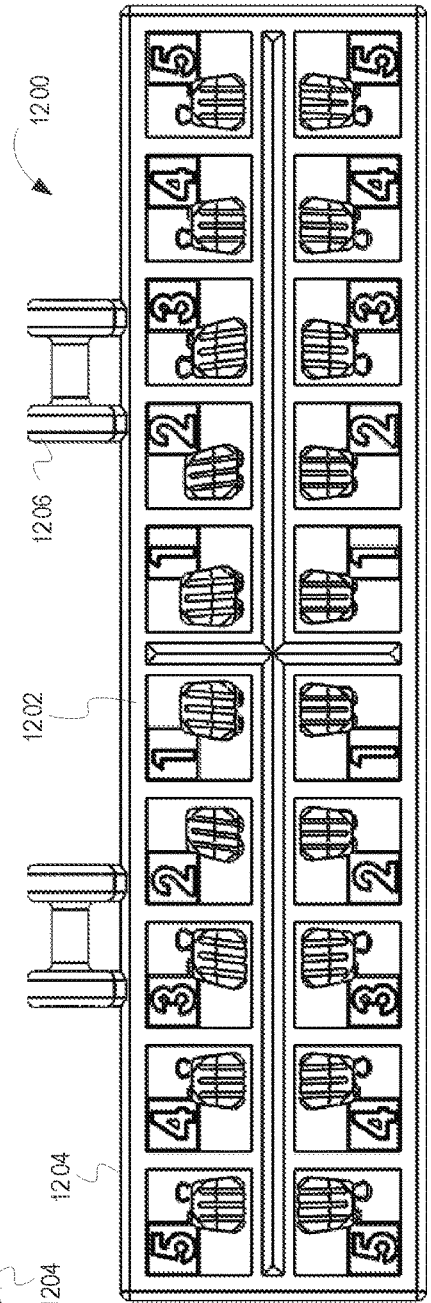

FIGS. 12A and 12B depict isometric and plan views, respectively, of base 1200 of a kit including orthodontic appliances, according to some embodiments. The base 1200 includes a number of subtrays 1204. Each of the subtrays 1204 includes an orthodontic appliance 1208. In one embodiments, the base 1200 and the orthodontic appliances 1208 are printed as a single unit. In such embodiments, each of the orthodontic appliances 1208 is affixed to the base 1200 via support structures 1210. The support structures 1210 elevate the orthodontic appliances 1208 off of the base 1200. In some embodiments, the joint between the support structures 1210 and the orthodontic appliances 1208 is frangible to facilitate easy separation of the orthodontic appliances 1208 from the base 1200. For example, the joint can be designed to fracture at a certain point and in a predictable and/or desired manner (e.g., across a line or other geometry). The base 1200 also includes hinges 1206. The hinges 1206 are designed to interface with a lid, as depicted in FIGS. 13A and 13B.

Figure 13A:
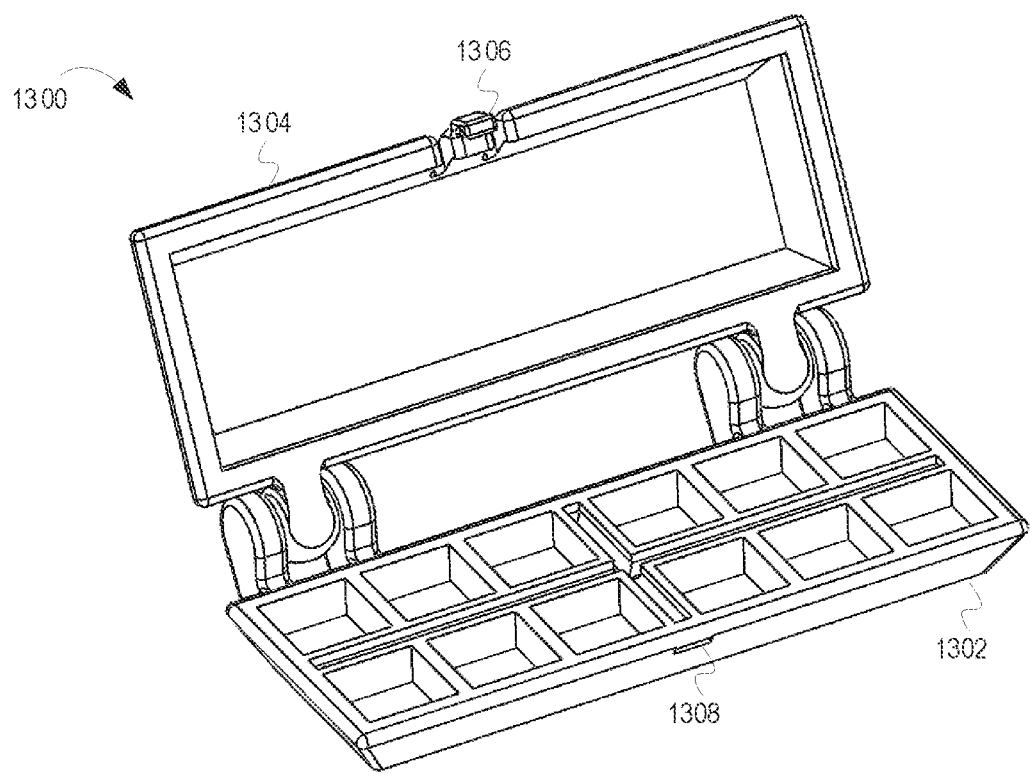
FIGS. 13A and 13B depicts a kit 1300 including orthodontic appliances having a base 1302 and a lid 1304, according to some embodiments.
Figure 13B:
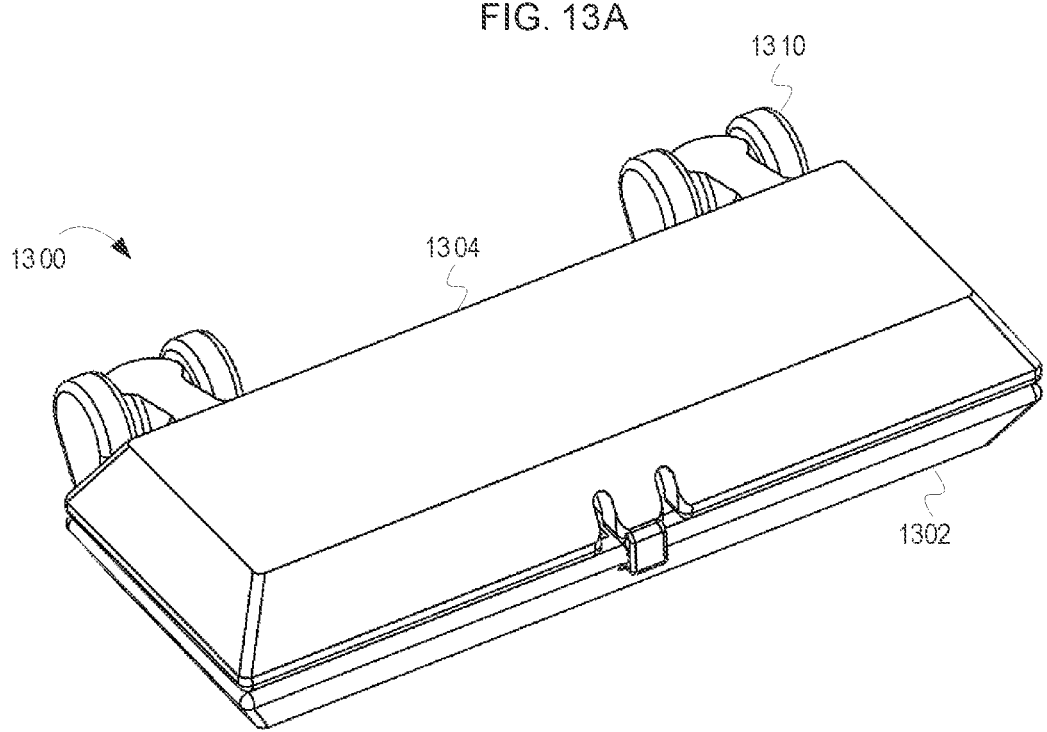

FIGS. 13A and 13B depicts a kit 1300 including orthodontic appliances having a base 1302 and a lid 1304, according to some embodiments. The lid 1304 is connected to the base via a hinge 1310. Though the kit 1300 depicted in FIGS. 13A and 13B is of a clamshell design, embodiments are not so limited. In some embodiments, the lid 1304 includes a latch 1306 capable of interfacing with a detent 1308.

While the discussion of FIGS. 12 and 13 provide additional detail regarding manufacture of sets of orthodontic appliances, the discussion of FIGS. 14-18 depict example orthodontic appliances having geometries that would be difficult, if not impossible, to produce using traditional manufacturing techniques.

Figure 14B:
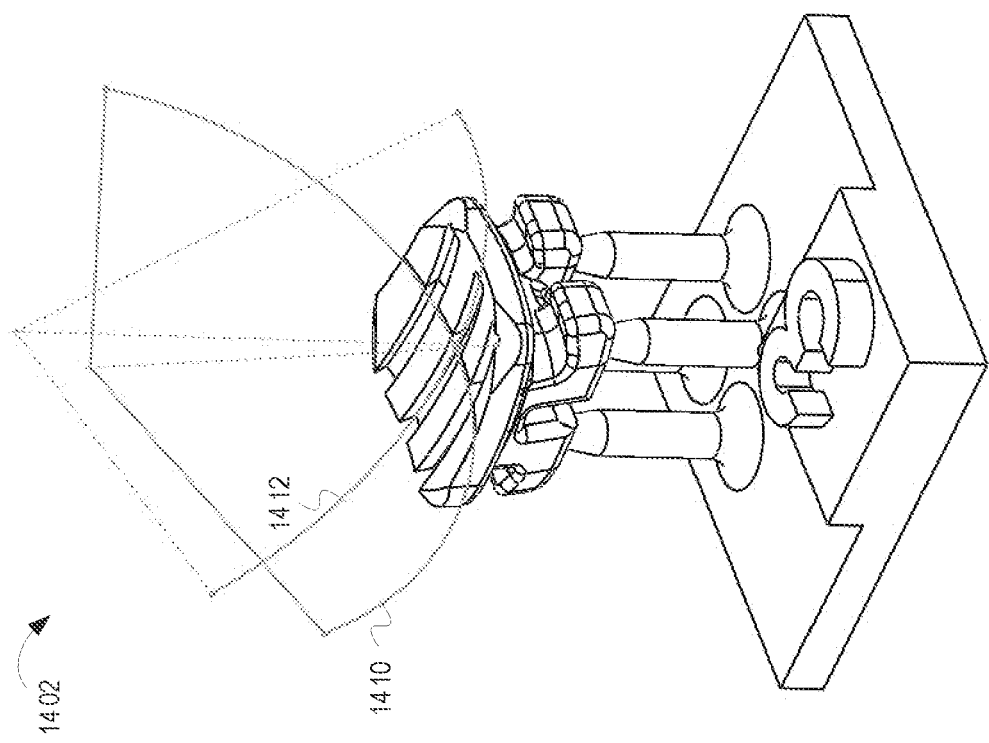
FIGS. 14A and 14B depict a bracket 1402 including a bonding surface 1408 that has a compound curvature, according to some embodiments.
Figure 14A:
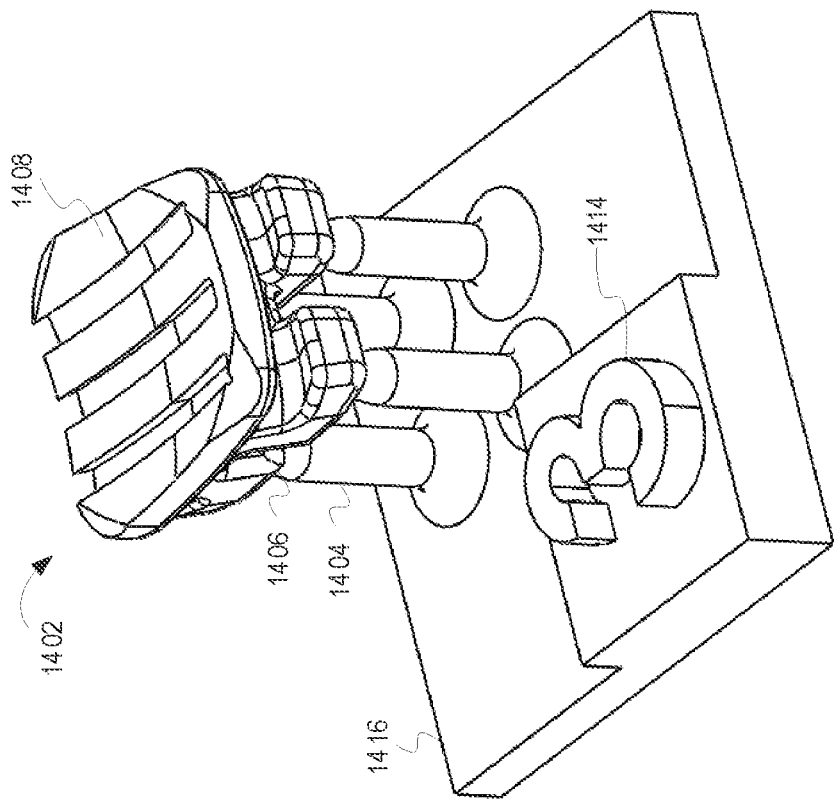

FIGS. 14A and 14B depict a bracket 1402 including a bonding surface 1408 that has a compound curvature, according to some embodiments. The bonding surface 1408 is the surface of the bracket 1402 that faces the patient's tooth. The surface of a patient's tooth is a compound contour in that it has multiple different radii, each radius oriented in a different plane. As depicted in FIGS. 14A and 14B, the bonding surface includes a compound curvature. The bonding surface 1408 includes a mesial-distal radius 1410 and an occlusal-gingival radius 1412. The mesial-distal radius 1410 and the occlusal-gingival radius 1412 are oriented in planes that are perpendicular to one another (e.g., the X-Z plane and the Y-Z plane). In some embodiments, a scan of the patient's mouth is used to model the bonding surface 1408 of the bracket 1402. That is, in some embodiments, the bonding surface 1408 of the bracket 1402 can be matched to fit the patient's tooth.

The bracket 1402 in FIGS. 14A and 14B is mounted on a support structure 1404. The support structure 1404 supports the bracket 1402 on a base 1416. The support structure 1404 and the bracket 1402 meet at a joint 1406. The support structure 1404 is configured to fracture at the joint 1406 so that the bracket 1402 can be removed from the base 1416. The bracket 1402 and the support structure 1404 can be separated by physically breaking the joint, severing the joint with an instrument such as a knife or scissors, etc. The base 1416 also include an identifier 1414. The identifier 1414 indicates with which tooth the bracket 1402 is to be paired.

FIG. 15 depicts a bracket 1502 including a dovetail 1504 through a bonding surface 1506 of the bracket 1502, according to some embodiments. The dovetail 1504 allows excess bonding material (e.g., adhesive) to flow from behind the bracket 1502. The dovetail 1504 follows the curvature of the bonding surface 1506. As with the bracket depicted in FIGS. 14A and 14B, the bonding surface 1506 of the bracket 1502 includes a compound curvature. Creation of such a dovetail in the curved bonding surface 1506 is extremely difficult, if not impossible, with traditional manufacturing techniques. However, such geometries are possible with additive manufacturing.

With traditional manufacturing techniques, the bracket 1502 at the bonding surface 1506 would need to be thicker to accommodate a dovetail that does not follow the compound curvature of the bonding surface 1506. Such thickness would place the bracket 1502 further from the facial axis of the tooth and result in compounding of tolerances. The end result would be less accurate placement and likely require additional adhesive.

Figure 16:
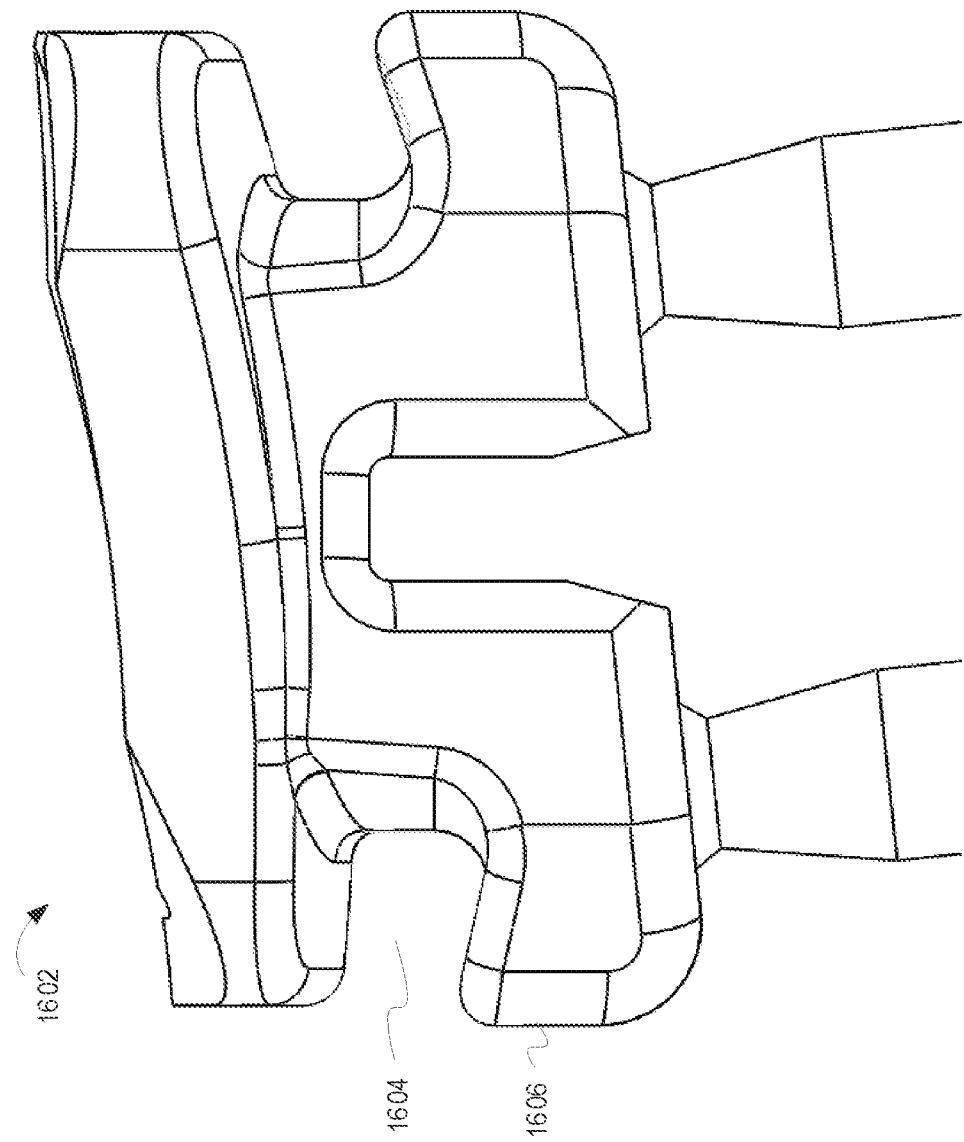
FIG. 16 is a side elevational view of a bracket 1602 depicting an undercut area 1604 of tiewings 1606, according to some embodiments.

FIG. 16 is a side elevational view of a bracket 1602 depicting an undercut area 1604 of tiewings 1606, according to some embodiments. Such an undercut area 1604 allows a ligature to be more easily secured on the bracket 1602. The ligature would typically be stretched about all four tiewings 1606, and the undercut area 1604 prevents the ligature from becoming unsecured from the tiewings 1606 as it is secured to the other tiewings 1606. Such undercuts are extremely difficult, if not impossible, to create with traditional manufacturing techniques.

Figure 17:
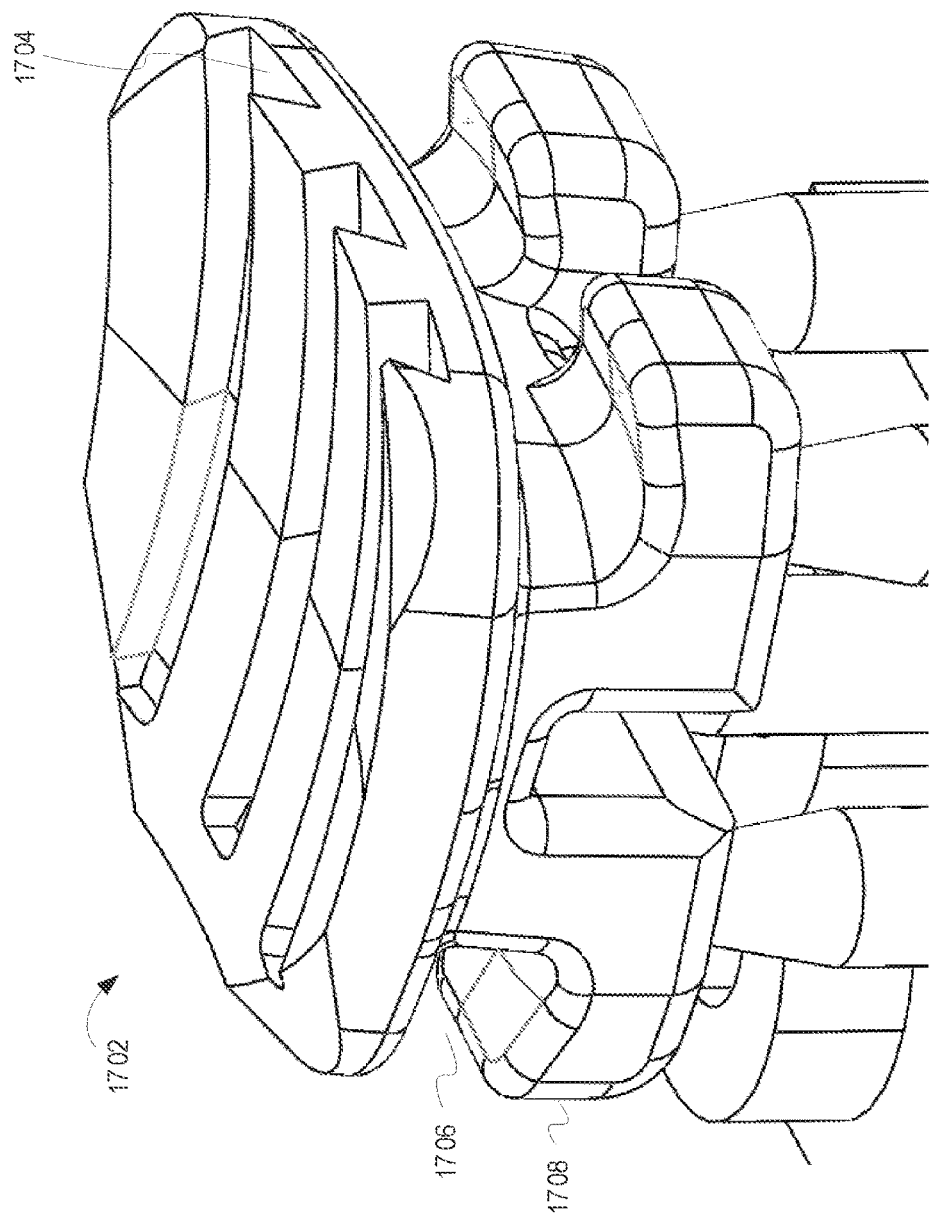
FIG. 17 is an isometric view of a bracket 1702 including dovetails 1704 and undercut areas 1706 of tiewings 1708, according to some embodiments.

FIG. 17 is an isometric view of a bracket 1702 including dovetails 1704 and undercut areas 1706 of tiewings 1708, according to some embodiments. Both the tiewings 1708 with undercut areas 1706 and the dovetail 1704 undercuts would be extremely difficult, if not impossible, to create with traditional manufacturing techniques.

Figure 18:
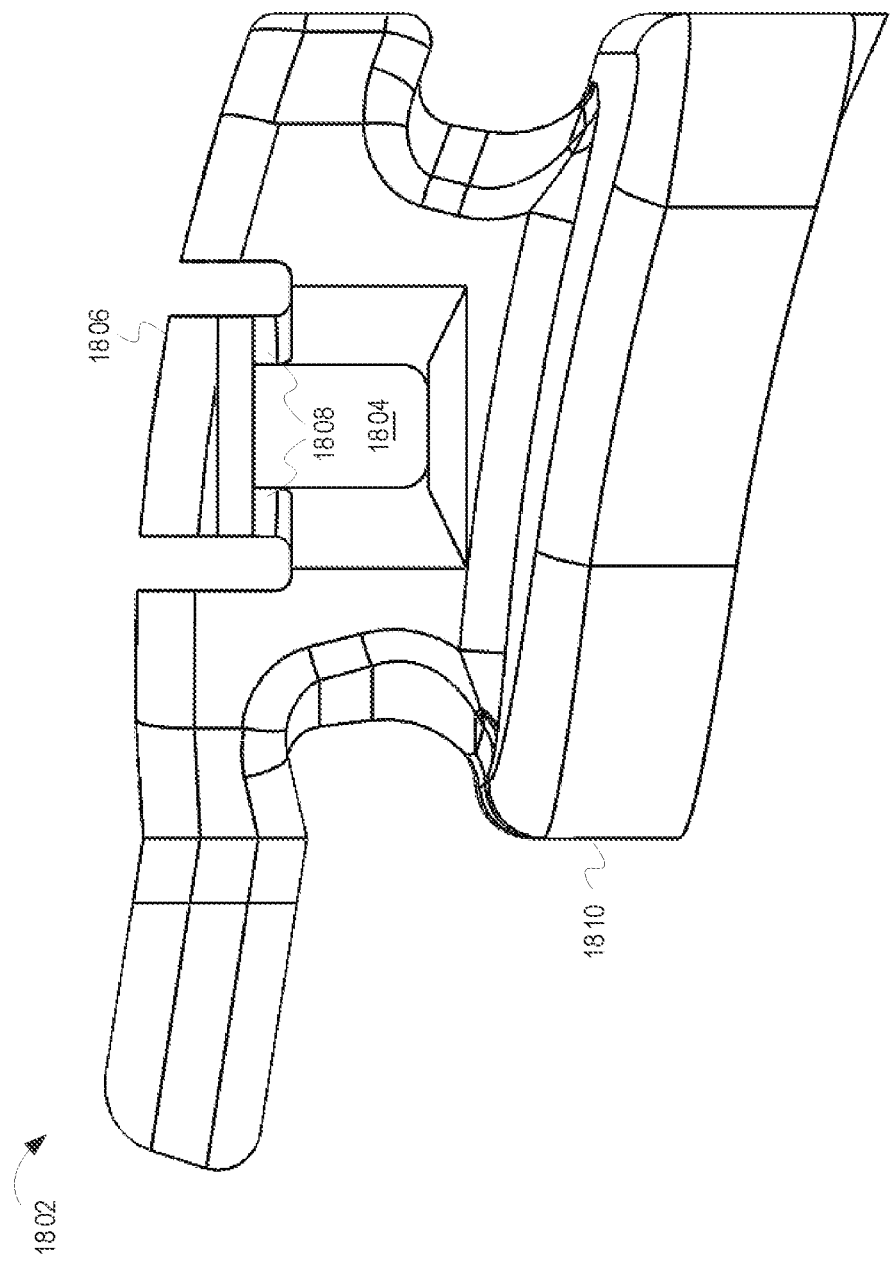
FIG. 18 depicts a convertible bracket 1802, according to some embodiments.

FIG. 18 depicts a convertible bracket 1802, according to some embodiments. The convertible bracket 1802 depicted in FIG. 18 is designed to be capable with, and without, an archwire. For example, at a first time during treatment, a clinician may not want to use an archwire with the convertible bracket 1802. However, as treatment progresses, use of the archwire may become beneficial. The clinician can anticipate this change and place the convertible bracket 1802 before use of the archwire is needed.

The convertible bracket 1802 includes an archwire slot 1804. The archwire slot 1804 is covered by a top structure 1806. The top structure 1806 closes off the archwire slot 1804 so that the bracket 1802 can be used without an archwire. If the clinician decides that he or she would like to use the bracket 1802 with an archwire, the top structure 1806 can be removed from the bracket 1802. The top structure 1802 meets the main bracket body 1810 at joints 1808. The joints 1808 are designed to allow the top structure 1806 to be removed from the main bracket body 1810 so that the archwire slot 1804 is exposed.

Traditionally, brackets that were capable of converting this way were made from multiple pieces of material. For example, a top structure would be manufactured independently of a main bracket body. The top structure would be welded or otherwise secured to the main bracket body. This type of manufacturing is expensive and difficult.

Figure 19:
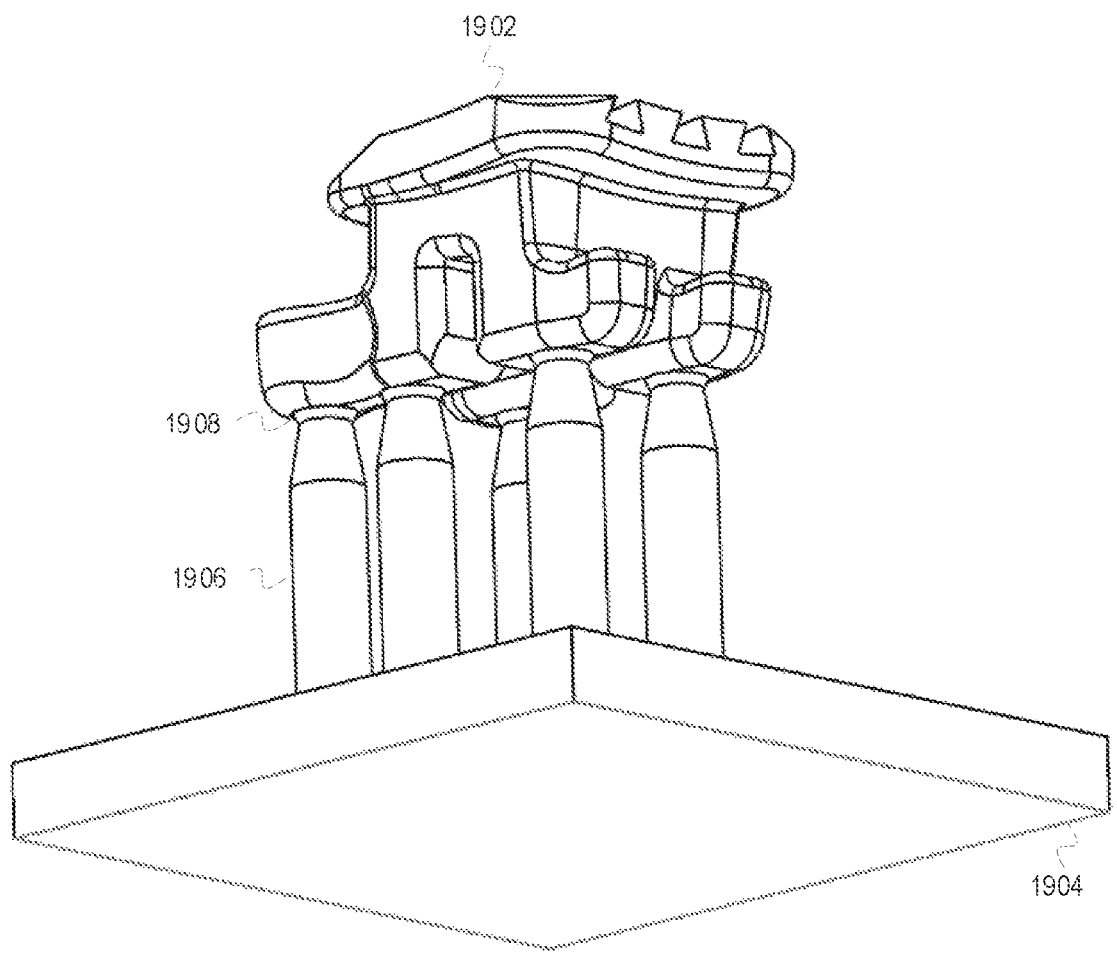
FIG. 19 is an isometric view of a bracket 1902 connected to a base 1904 via support structures 1906, according to some embodiments.

While the discussion of FIGS. 14-18 describes bracket geometries and/or styles that are unique to the systems, methods, and apparatus described herein, the discussion of FIGS. 19-20 describes manufacture of orthodontic appliances and bases.

FIG. 19 is an isometric view of a bracket 1902 connected to a base 1904 via support structures 1906, according to some embodiments. In some embodiments, the bracket 1902, the support structures 1906, and the base 1904 are manufactured (e.g., printed) as a single unit). The support structures 1906 join the bracket 1902 to the base 1904 at a joint 1908. In one embodiment, the joint 1908 has a double taper configuration. In the double taper configuration, both ends of the joint 1908 taper to a section that is, for example, thinner than the rest of the support structure 1906 or otherwise includes less material than the rest of the support structure 1906. The thinning of the support structure 1906 at the joint 1908 allows the bracket 1902 to be detached from the base 1904 by a user via physical input. The geometry of the joint 1908 focuses stress from physical manipulation of the bracket 1902 and/or base 1904 at a desired location within the joint 1908. Accordingly, such joint 1908 geometry allows for a clean fracture of the material at, or near, the joint 1908.

Additionally, in some embodiments, the locations, numbers, positions, etc. of the support structures 1906 can be user-defined. For example, the user can select precise locations of the support structures 1906 based on the geometry of the bracket 1902. In such embodiments, the support structures 1906 can be included in the data file for the bracket 1902. This provides the user with ability to locate the support structures 1906 as desired to facilitate clean and/or easier separation of the bracket 1902 from the base 1904.

Figure 20A:
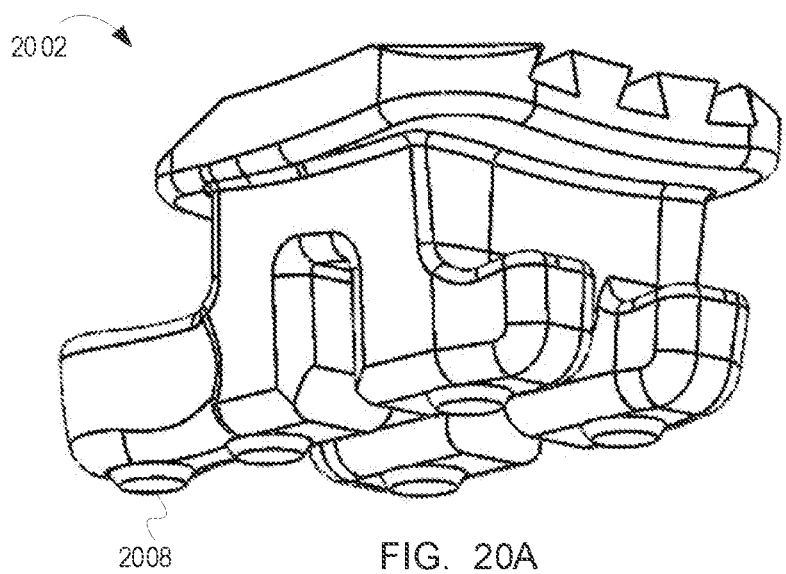
FIG. 20A is an isometric view of a bracket 2002, according to some embodiments.
Figure 20B:
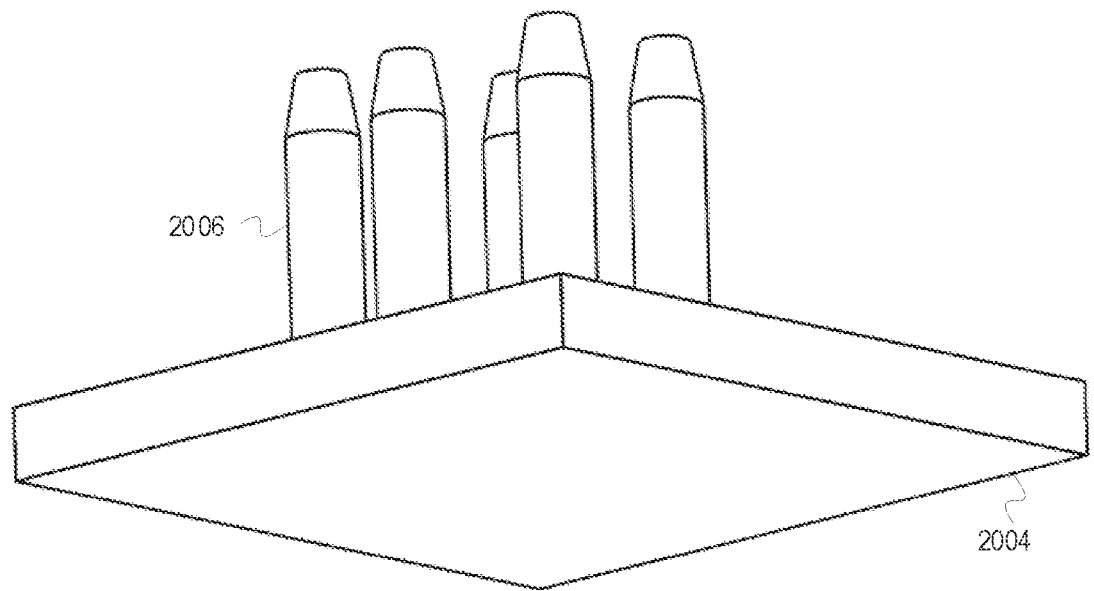
FIG. 20B is an isometric view of a base 2004, according to some embodiments.

FIG. 20A is an isometric view of a bracket 2002, according to some embodiments. FIG. 20B is an isometric view of a base 2004, according to some embodiments. As depicted between FIGS. 20A and 20B, the bracket 2002 is severable from the support structures 2006, and thus the base 2004. In the example provided in FIGS. 20A and 20B, the placement of the support structures 2006 and the joints is such that nubs 2008 remain on the bracket 2002 when the bracket 2002 is removed from the base 2004.

In some embodiments, a system for providing data files associated with orthodontic appliances comprises a database, wherein the database stores the data files associated with the orthodontic appliances and a control circuit, wherein the control circuit is communicatively coupled to the database, a user device, and a printer, wherein the control circuit is configured to receive, from the user device, an indication of a selected orthodontic device, retrieve, based on the indication of the selected orthodontic device from the database, one of the data files associated with the orthodontic appliances, wherein the one of the data files associated with the orthodontic appliances corresponds to the selected orthodontic appliance, and transmit, to the printer, the one of the data files associated with the orthodontic appliances.

In some embodiments, the system further comprises the user device, wherein the user device includes a display device, wherein the display device is configured to present, to a user, a catalogue, wherein the catalogue include the orthodontic appliances, a user input device, wherein the user input device is configured to receive, from the user, a selection of the selected orthodontic appliance, and a communications radio, wherein the communications radio is configured to transmit, to the control circuit, the indication of the selected orthodontic appliance.

In some embodiments, the user input device is further configured to receive, from the user, user input to modify base versions of the orthodontic appliances, and wherein the selected orthodontic appliance is a modified version of a base version of the selected orthodontic appliance.

In some embodiments, the user input to modify the base versions of the orthodontic appliances includes one or more of modifying a slot width, a tip angulation, a tongue angulation, an offset angulation, a mesial-distal width, an occlusal-gingival height, an in-out height, a mesial-distal base radius, an occlusal-gingival base radius, a type of hook, a presence of a hook, and a location of a hook.

In some embodiments, the system further comprises the manufacturing device, wherein the manufacturing device is configured to receive, from the control circuit, the one of the data files associated with the orthodontic appliances, and manufacture, based on the one of the data files associated with the orthodontic appliances, the selected orthodontic appliance.

In some embodiments, the manufacturing device is a printer, and the manufacturing device is further configured to verify, before printing the selected orthodontic appliance, that a resin installed in the printer is compatible with the selected orthodontic appliance.

In some embodiments, the one of the data files associated with the orthodontic appliances includes an indication of compatible resins, and wherein the manufacturing device verifies that the resin installed in the manufacturing device is compatible with the selected orthodontic appliance based on the one of the data files associated with the orthodontic appliances.

In some embodiments, a system for additively manufacturing orthodontic appliances comprises a database storing data files associated with the orthodontic appliances, a user device, wherein the user device includes a display device, wherein the display device is configured to present, to a user, a catalogue, wherein the catalogue includes the orthodontic appliances, a user input device, wherein the user input device is configured to receive, from the user, a selection of one of the orthodontic appliances, and a communications radio, wherein the communications radio is configured to transmit, via a network, an indication of the one of the orthodontic appliances, a control circuit, wherein the control circuit is configured to receive, via the network from the user device, the indication of the one of the orthodontic appliances, retrieve, from the database, one of the data files associated with the orthodontic appliances, wherein the one of the data files associated with the orthodontic appliances corresponds to the indication of the one of the orthodontic appliances, and transmit, via the network to a manufacturing device, the one of the data files associated with the orthodontic appliances, and the manufacturing device, wherein the manufacturing device is configured to receive, via the network from the control circuit, the one of the data files associated with the orthodontic appliances, and additively manufacture, based on the one of the data files associated with the orthodontic appliances, the one of the orthodontic appliances.

In some embodiments, an apparatus and a corresponding method performed by the apparatus comprises generating data files, wherein the data files are associated with the orthodontic appliances, storing, in a database, the data files, presenting, by a display device of a user device, a catalogue, wherein the catalogue includes the orthodontic appliances, receiving, by a user input device of the user device, a selection of one of the orthodontic appliances, transmitting, by a communications radio of the user device, an indication of the one of the orthodontic appliances, receiving, by a control circuit via a network, the indication of the one of the orthodontic appliances, retrieving, by the control circuit from the database, one of the data files, wherein the one of the data files corresponds to the indication of the one of the orthodontic appliances, transmitting, by the control circuit via the network, the one of the data files, receiving, by a manufacturing device via the network, the one of the data files, and additively manufacturing, by the manufacturing device based on the one of the data files, the one of the orthodontic appliances.

In some embodiments, a system for additively manufacturing orthodontic appliances comprises a database storing data files associated with the orthodontic appliances, a user device, wherein the user device includes a display device, wherein the display device is configured to present, to a user, a catalogue, wherein the catalogue includes the orthodontic appliances, a user input device, wherein the user input device is configured to receive, from the user, a selection of one of the orthodontic appliances, and a communications radio, wherein the communications radio is configured to transmit, via a network, an indication of the one of the orthodontic appliances, a control circuit, wherein the control circuit is configured to receive, via the network from the user device, the indication of the one of the orthodontic appliances, retrieve, from the database, one of the data files associated with the orthodontic appliances, wherein the one of the data files associated with the orthodontic appliances corresponds to the indication of the one of the orthodontic appliances, and transmit, via the network to the user device, the one of the data files associated with the orthodontic appliances, and the manufacturing device, wherein the manufacturing device is configured to receive, via the network from the user device, the one of the data files associated with the orthodontic appliances, and additively manufacture, based on the one of the data files associated with the orthodontic appliances, the one of the orthodontic appliances.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for additively manufacturing orthodontic appliances, the system comprising:
   a database storing data files associated with the orthodontic appliances, wherein the data files are generated for base orthodontic appliances and modified orthodontic appliances, and wherein each of the modified orthodontic appliances is a permutation of one of the base orthodontic appliances;
   a user device, wherein the user device includes:
      a display device, wherein the display device is configured to:
         present, to a user, a catalogue, wherein the catalogue includes the orthodontic appliances;
      a user input device, wherein the user input device is configured to:
         receive, from the user, a selection of one of the orthodontic appliances; and
      a communications radio, wherein the communications radio is configured to:
         transmit, via a network, an indication of the one of the orthodontic appliances;
   a control circuit, wherein the control circuit is configured to:
      receive, via the network from the user device, the indication of the one of the orthodontic appliances;
      determine, based on the indication of the one of the orthodontic appliances, one of the base orthodontic appliances that corresponds to the one of the orthodontic appliances;
      select, based on the indication of the one of the orthodontic appliances and the one of the base orthodontic appliances, one of the modified orthodontic appliance;
      retrieve, from the database, one of the data files associated with the one of the modified orthodontic appliances; and
      transmit, via the network to a manufacturing device, the one of the data files associated with the one of the modified orthodontic appliances; and
   the manufacturing device, wherein the manufacturing device is configured to:
      receive, via the network from the control circuit, the one of the data files associated with the one of the modified orthodontic appliances; and
      additively manufacture, based on the one of the data files associated with the one of the modified orthodontic appliances, the one of the orthodontic appliances.

2. The system of claim 1, wherein the control circuit and database are located remotely from the user device and the manufacturing device.

3. The system of claim 1, wherein the selection of one of the orthodontic appliances includes a modification to a base version of the one of the orthodontic appliances.

4. The system of claim 3, wherein the modification to the base version of the one of the orthodontic appliances includes one or more of modifying a slot width, a tip angulation, a tongue angulation, an offset angulation, a mesial-distal width, an occlusal-gingival height, an in-out height, a mesial-distal base radius, an occlusal-gingival base radius, a type of hook, a presence of a hook, and a location of a hook.

5. The system of claim 1, wherein each of the modified orthodontic appliances is a permutation of one of the base orthodontic appliances in that that the modified orthodontic appliances are permutations based on modifiable parameters for each base orthodontic appliance.

6. The system of claim 1, wherein the database includes indications of resins that are compatible with each of the data files associated with the orthodontic appliances, and wherein the manufacturing device is further configured to:
   verify, based on the indications of resins that are compatible with each of the data files associated with the orthodontic appliances before additively manufacturing the one of the orthodontic appliances, that an installed resin is compatible with the one of the data files associated with the orthodontic appliances.

7. The system of claim 1, wherein the one of the orthodontic appliances is a direct-bonded orthodontic appliance.

8. A method for additively manufacturing orthodontic appliances, the method comprising:
   generating data files, wherein the data files are associated with the orthodontic appliances, wherein the data files include base orthodontic appliances and modified orthodontic appliances, and wherein each of the modified orthodontic appliances is a permutation of one of the base orthodontic appliances;

storing, in a database, the data files;

presenting, by a display device of a user device, a catalogue, wherein the catalogue includes the orthodontic appliances;

receiving, by a user input device of the user device, a selection of one of the orthodontic appliances;

transmitting, by a communications radio of the user device, an indication of the one of the orthodontic appliances;

receiving, by a control circuit via a network, the indication of the one of the orthodontic appliances;

determining, by the control circuit based on the indication of the one of the orthodontic appliances, one of the base orthodontic appliances that corresponds to the one of the orthodontic appliances;

selecting, by the control circuit based on the indication of the one of the orthodontic appliances and the one of the base orthodontic appliances, one of the modified orthodontic appliances;

retrieving, by the control circuit from the database, one of data files, wherein the one of data files corresponds to the one of the modified orthodontic appliances;

transmitting, by the control circuit via the network, the one of the data files;

receiving, by a manufacturing device via the network, the one of the data files; and additively manufacturing, by the manufacturing device based on the one of the data files, the one of the orthodontic appliances.

9. The method of claim 8, further comprising:

receiving, by the user input device, user input to modify the one of the orthodontic appliances, wherein the user input includes selection to modify one or more parameters associated with the one of the orthodontic appliances.

10. The method of claim 9, wherein the parameters associated with the one of the orthodontic appliances include one or more of a slot width, a tip angulation, a tongue angulation, an offset angulation, a mesial-distal width, an occlusal-gingival height, an in-out height, a mesial-distal base radius, an occlusal-gingival base radius, a type of hook, a presence of a hook, and a location of a hook.

11. The method of claim 8, wherein the orthodontic appliances include a set of base appliances, wherein each of the base appliances can be modified, and wherein the data files include data files for each of the base appliances and data files for each permutation of each of the base appliances each of the modified orthodontic appliances is a permutation of one of the base orthodontic appliances in that the modified orthodontic appliances are permutations based on modifiable parameters for each of the base orthodontic appliances.

12. The method of claim 8, further comprising:

verifying, by the manufacturing device before additively manufacturing the one of the orthodontic appliances, that an installed resin is compatible with the one of the orthodontic appliances.

13. The method of claim 8, wherein the one of the orthodontic appliances is a direct-bonded orthodontic appliance.

14. The method of claim 8, wherein the control circuit transmits the one of the data files to the user device, and wherein the manufacturing device receives the one of the data files from the user device.

15. The method of claim 8, wherein the control circuit transmits the one of the data files to the manufacturing device.

16. A system for additively manufacturing orthodontic appliances, the system comprising:

a database storing data files associated with the orthodontic appliances, wherein the data files are generated for base orthodontic appliances and modified orthodontic appliances, and wherein each of the modified orthodontic appliances is a permutation of one of the base orthodontic appliances;

a user device, wherein the user device includes:

a display device, wherein the display device is configured to:

present, to a user, a catalogue, wherein the catalogue includes the orthodontic appliances;

a user input device, wherein the user input device is configured to:

receive, from the user, a selection of one of the orthodontic appliances; and a communications radio, wherein the communications radio is configured to:

transmit, via a network, an indication of the one of the orthodontic appliances;

a control circuit, wherein the control circuit is configured to:

receive, via the network from the user device, the indication of the one of the orthodontic appliances;

determine, based on the indication of the one of the orthodontic appliances, one of the base orthodontic appliances that corresponds to the one of the orthodontic appliances;

select, based on the indication of the one of the orthodontic appliances and the one of the base orthodontic appliances, one of the modified orthodontic appliance;

retrieve, from the database, one of the data files associated with the one of the modified orthodontic appliances; and transmit, via the network to the user device, the one of the data files associated with the one of the modified orthodontic appliances; and a manufacturing device, wherein the manufacturing device is configured to:

receive, via the network from the user device, the one of the data files associated with the one of the modified orthodontic appliances; and additively manufacture, based on the one of the data files associated with the one of the modified orthodontic appliances, the one of the orthodontic appliances.

17. The system of claim 16, wherein the control circuit and database are located remotely from the user device and the manufacturing device.

18. The system of claim 16, wherein the selection of one of the orthodontic appliances includes a modification to a base version of the one of the orthodontic appliances.

19. The system of claim 18, wherein the modification to the base version of the one of the orthodontic appliances includes one or more of modifying a slot width, a tip angulation, a tongue angulation, an offset angulation, a mesial-distal width, an occlusal-gingival height, an in-out height, a mesial-distal base radius, an occlusal-gingival base radius, a type of hook, a presence of a hook, and a location of a hook.

20. The system of claim 16, wherein each of the modified orthodontic appliances is a permutation of one of the base orthodontic appliances in that that the modified orthodontic appliances are permutations based on modifiable parameters for each base orthodontic appliance.

21. The system of claim 16, wherein the database includes indications of resins that are compatible with each of the data files associated with the orthodontic appliances, and wherein the manufacturing device is further configured to:
verify, based on the indications of resins that are compatible with each of the data files associated with the orthodontic appliances before additively manufacturing the one of the orthodontic appliances, that an installed resin is compatible with the one of the data files associated with the orthodontic appliances.

22. The system of claim 16, wherein the database includes indications of resins that are compatible with each of the data files associated with the orthodontic appliances, and wherein the user device is further configured to:
verify, based on the indications of resins that are compatible with each of the data files associated with the orthodontic appliances before the additive manufacturing of the one of the orthodontic appliances, that an installed resin is compatible with the one of the data files associated with the orthodontic appliances.

23. The system of claim 16, wherein the control circuit is further configured to:
encode each of the data files with one-time use encryption, wherein the one-time use encryption allows a single access to a data file for a key.

24. The system of claim 16, wherein the one of the orthodontic appliances is a direct-bonded orthodontic appliance.

\* \* \* \* \*